(12) United States Patent
Khaghani et al.

(10) Patent No.: US 6,984,201 B2
(45) Date of Patent: Jan. 10, 2006

(54) BLOOD CIRCULATION ASSISTANCE DEVICE

(75) Inventors: Asghar Khaghani, Amersham (GB); Geoffrey Thomas Andrews, Cambridge (GB); Christopher Bowles, Croxley Green (GB); Nigel Gordon Smith, Barley (GB)

(73) Assignee: Harefield Cardiac Limited, London (GB)

( * ) Notice: Subject to any disclaimer, the term of this patent is extended or adjusted under 35 U.S.C. 154(b) by 1 day.

(21) Appl. No.: 10/395,706

(22) Filed: Mar. 24, 2003

(65) Prior Publication Data

US 2003/0233023 A1 Dec. 18, 2003

Related U.S. Application Data

(63) Continuation of application No. PCT/GB01/04250, filed on Sep. 24, 2001.

(30) Foreign Application Priority Data

Sep. 23, 2000 (GB) .................................... 0023412

(51) Int. Cl.
*A61N 1/362* (2006.01)

(52) U.S. Cl. ...................................................... 600/17

(58) Field of Classification Search ............. 600/16–18
See application file for complete search history.

(56) References Cited

U.S. PATENT DOCUMENTS

| 4,014,318 A | 3/1977 | Dockum et al. |
| 4,131,604 A | 12/1978 | Szycher ........................ 528/79 |
| 4,245,622 A | 1/1981 | Hutchins, IV ............. 128/1 D |
| 4,583,523 A | 4/1986 | Kleinke et al. ............. 128/1 D |
| 4,633,120 A | 12/1986 | Sato et al. ................... 310/328 |
| 4,979,936 A | 12/1990 | Stephenson et al. .......... 600/16 |
| 5,136,201 A | 8/1992 | Culp ........................... 310/328 |
| 5,215,446 A | 6/1993 | Takahashi et al. .......... 417/322 |
| 5,222,980 A | 6/1993 | Gealow .......................... 623/3 |

(Continued)

FOREIGN PATENT DOCUMENTS

DE 3538718 4/1987

(Continued)

OTHER PUBLICATIONS

Cernaianu et al., "Latissimus Dorsi and Serratus Anterior Dynamic Descending Aortomyoplasty for Ischemic Cardiac Failure", *Ann. Thorac. Surg.*, 1995; 59: 639-43.

(Continued)

*Primary Examiner*—Mark Bockelman
(74) *Attorney, Agent, or Firm*—Heslin Rothenberg Farley & Mesiti, P.C.; Victor A. Cardona, Esq.

(57) ABSTRACT

A blood circulation assistance device (1), for location around a blood conduit (20). The device comprises: an inflatable bladder (10) moveable between a contracted form and an expanded form, for compressing the blood conduit (20) to provide counterpulsation. Pump means (30) in fluid communication with the bladder (10) move the bladder (10) from the contracted form to the expanded form. The pump means (30) comprises a centrifugal impeller (62) rotatable about an axis (61) to effect pumping. The impeller (62) is moveable axially between first and second positions to effect a reversal of the direction of pumping. Control means (50), in communication with the pump means, is capable of monitoring the cardiac cycle of an individual and triggering the pump means (30) to move the bladder (10) to the expanded form at diastole. An outer cuff, surrounds at least a portion of the bladder (10), providing an outer limiting extent to the movement of the bladder (10).

61 Claims, 12 Drawing Sheets

U.S. PATENT DOCUMENTS

| | | | | |
|---|---|---|---|---|
| 5,273,518 | A | 12/1993 | Lee et al. | 600/16 |
| 5,318,501 | A | 6/1994 | Lee et al. | 600/16 |
| 5,346,458 | A | 9/1994 | Affeld | 600/16 |
| 5,429,584 | A | 7/1995 | Chiu | 600/18 |
| 5,713,954 | A | 2/1998 | Rosenberg et al. | 623/3 |
| 6,045,496 | A | 4/2000 | Pacella et al. | 600/16 |
| 6,084,321 | A | 7/2000 | Hunter et al. | 310/20 |
| 6,109,852 | A | 8/2000 | Shahinpoor et al. | 414/1 |
| 6,111,818 | A | 8/2000 | Bowen et al. | 367/140 |
| 6,186,149 | B1 | 2/2001 | Pacella et al. | 128/898 |
| 6,249,076 | B1 | 6/2001 | Madden et al. | 310/363 |
| 6,808,484 | B1 * | 10/2004 | Peters et al. | 600/18 |
| 2003/0032854 | A1 | 2/2003 | Palmer | 600/16 |

FOREIGN PATENT DOCUMENTS

| | | |
|---|---|---|
| EP | 0590158 | 4/1993 |
| FR | 1562754 | 1/1966 |
| GB | 1220677 | 3/1971 |
| GB | 2036371 | 11/1979 |
| GB | 2322232 | 8/1998 |
| WO | WO 91/08003 | 6/1991 |
| WO | WO 92/10916 | 6/1992 |
| WO | WO 93/05827 | 4/1993 |
| WO | WO 94/06395 | 3/1994 |
| WO | WO 95/28127 | 10/1995 |
| WO | WO 97/26929 | 7/1997 |
| WO | WO 97/49439 | 12/1997 |
| WO | WO 98/00185 | 1/1998 |
| WO | WO 98/03212 | 1/1998 |
| WO | WO 98/17347 | 4/1998 |
| WO | WO 99/04833 | 2/1999 |
| WO | WO 99/16481 | 4/1999 |
| WO | WO 99/17929 | 4/1999 |
| WO | WO 99/22784 | 5/1999 |
| WO | WO 99/26675 | 6/1999 |
| WO | WO 00/32256 | 6/2000 |
| WO | WO 00/43053 | 7/2000 |
| WO | WO 00/43054 | 7/2000 |
| WO | WO 00/76288 | 12/2000 |
| WO | WO 01/47041 | 6/2001 |
| WO | WO 01/47318 | 6/2001 |
| WO | WO 01/66170 | 9/2001 |
| WO | WO 02/24255 | 3/2002 |
| WO | WO 03/011365 | 2/2003 |

OTHER PUBLICATIONS

Carpenter et al., "Myocardial Substitution With a Stimulated Skeletal Muscle: First Successful Clinical Case", *The Lancet*, 1985; p 1267.

Chachques et al., "Long-Term Effects of Dynamic Aortomyoplasty", *Ann. Thorac. Surgery*, 1994; 58: 128-34.

Clauss et al., "The Arterial Counterpulsator", *J. of Thoracic & Cardiovas. Surg.*, 1961; 42: 447-58.

Flum et al., "Descending Thoracic Aortomyoplasty: A Technique for Clinical Application", *Ann. Thorac. Surg.*, 1996; 61: 93-8.

Hayward et al., "Myoplasty—a surgical option for end-stage heart failure", *British Journal of Hospital Medicine*, 1995; vol. 53, No. 9: 435-38.

Fischer et al., "Benefits of Aortic and Pulmonary Counterpulsation Using Dynamic Latissimus Dorsi Myoplasty", *Ann. Thorac. Surg.*, 1995; 60:417-21.

Lazzara et al., "Dynamic Descending Thoracic Aortomyoplasty: Comparison With Intraaortic Balloon Pump in a Model of Heart Failure", *Ann. Thorac. Surg.* 1994; 58:366-71.

Lazzara et al., " Autogenous Cardiac Assist With Chronic Descending Thoracic Aortomyoplasty", *Ann. Thorac. Surg.*, 1994; 57:1540-4.

Mitsumaru et al., "Experimental Study of Combination of Extraaortic Balloon Counterpulsation and Ventricular Assist Cup to Acute Heart Failure in Dogs", *ASAIO Journal*, 1997; 43: 187-92.

Moulopoulos et al., "Diastolic balloon pumping (with carbon dioxide) in the aorta—A mechanical assistance to the failing circulation", *Am. Heart J.*, May 1962; 669-75.

Mundth, Eldred D., "Assisted Circulation", *The Coronary Circulation*, 1983; 1490-1514.

Odaguchi et al., "Experimental Study of Extraaortic Balloon Counterpulsation as a Bridge to Other Mechanical Assists", *ASAIO Journal* 1996; vol. 42, No. 3: 190-4.

Ohman et al., "Use of Aortic Counterpulsation to Improve Sustained Coronary Artery Patency During Acute Myocardial Infarction", *Circulation* , 1994; vol. 90, No. 2: 792-9.

Perez-Tamayo et al., "Prolonged Total Circulatory Support Using Direct Mechanical Ventricular Actuation", *Direct Mechanical Ventricular Actuation* , 1995; 41: M512-M517.

Rosenbaum et al., Intra-aortic Balloon Counterpulsation as a 'Bridge' to Cardiac Transplantation, *Chest*, Dec. 1994; 106, 6:1638-8.

Segers et al., "Role and Relevancy of a Cardiovascular Simulator", *Cardiovascular Engineering*, Apr. 1988; vol. 3, No. 1: 48-56.

* cited by examiner

BLOOD CIRCULATION ASSISTANCE DEVICE

CROSS REFERENCE TO RELATED APPLICATIONS

This application is a continuation of International Application No. PCT/GB01/04250, filed on Sep. 24, 2001, and published in English on Mar. 28, 2002, as WO 02/24254 A2, which claims priority from Great Britain patent application GB 0023412.0, filed on Sep. 23, 2000, the entire disclosures of which are incorporated herein by reference.

The present invention relates to a blood circulation assistance device and, in particular, a blood circulation assistance device capable of effecting counterpulsation.

Cardiac assist devices can help relieve the load on the heart and increase cardiac output. One type of cardiac assist device are those that effect counterpulsation. A variety of counterpulsation methods have been described for the treatment of acute and end-stage heart failure. The dual benefits of counterpulsation are improved systemic organ perfusion (notably the myocardium) during diastole and left ventricular afterload reduction. In order for counterpulsation to be effective, it is necessary to displace as large a volume of blood as is practicable from the systemic arteries (notably the aorta) at the beginning of diastole and to reverse this process prior to subsequent systole.

Typical devices include the intra-aortic balloon (IAB) counterpulsator, extra ventricular assist devices and Latissimus dorsi myoplasty. As such they are very useful for a wide range of patients, especially those rated as NYHA (New York Health Authority) Grades III and IV. Aortic counterpulsation was initially conceived by Clauss[1] (1961) and the intra-aortic balloon introduced in 1962 by Moulopoulos[2]. Despite its usefulness[3] the IAB device has a number of shortcomings that reduce its usefulness and long-term viability. The IAB device is highly invasive, requiring trans femoral catheterisation and provides the opportunity for infection and thrombogenic complications. In particular, intra-aortic balloon counterpulsation is associated with significant complications, notably, thromboembolism, infection and leg ischaemia. Moreover the system is non-ambulatory, only suitable for short support periods, and there is a risk of balloon perforation leading to gaseous arterial embolisation. As such, IABs are limited to hospital in-patients, particularly those in intensive care.

Since the development of the IAB, direct mechanical compression of the heart for circulatory assistance has been developed after Hayward[4] and Fischer[5]. However these techniques are relatively unproven, highly invasive, expensive and inapplicable to high-risk patients due to the possibly lethal trauma of surgery and the lack of any immediate benefit, despite their need for such an effect.

For almost two decades, mobilised and pulse-train stimulated skeletal muscle has been proposed as a method for effecting counterpulsation either by wrapping it around the aorta (aortomyoplasty) or by fashioning pouches or shunts in communication with the aorta.

For example, WO-A-93/05827 discloses an implantable heart-assist device comprising an extra-aortic balloon pump for insertion into a patient's vascular system. The extra-aortic balloon pump is powered by contraction of a skeletal muscle pouch connected to the balloon. Similarly, U.S. Pat. No. 4,979,936 discloses an autologous biologic pump motor comprising an expanding bladder located around a portion of an individual's aorta. The expanding bladder is powered by contraction of skeletal muscle surrounding a collapsible bladder that is connected to the expanding bladder.

The problem with these arrangements is that, in practice, the devices do not pump a sufficient volume of blood to assist a patient. This is because the devices use stimulated skeletal muscle and there is inadequate sustained power and suboptimal contraction and relaxation times using muscle as an actuator. Furthermore, since the devices rely on stimulated skeletal muscle, there is a requirement for a period of delay before the muscle can be utilised effectively,.

Recently, counterpulsation methods employing indirect electrohydraulic actuation have been disclosed such as in WO-A-99/04833. This document discloses a centrifugal or ferrofluid type pump for the transit of the fluid drive medium. However, this document does not disclose how the flow of hydraulic drive medium is reversed, which is important for providing effective counterpulsation.

The present invention seeks to alleviate one or more of the above problems.

The present inventor has overcome the disadvantages of the prior art, providing an implantable, minimally invasive extravascular aortic counter pulsator device which does not require direct blood contact, may be used for ambulatory purposes, and which provides an immediate benefit whilst minimising the possibility of infection or thrombogenic complications due to the lack of direct blood contact.

According to the present invention there is provided an extravascular aortic counterpulsator device comprising actuator means for compressing a blood vessel and control means for controlling the timing of the compression of the blood vessel by the actuator means.

The counterpulsator device may be an aortic diastolic counterpulsator device.

The actuator means may for example comprise a peri-aortic jacket that surrounds the aorta, or a sutured reinforced open weave vascular graft (for example Dacron™, known generically as polyester or polyethylene tetraphthalate (PET)) to replace or augment or protect diseased aorta, and having an expandable balloon interior and a relatively rigid exterior, and pump means attached to the control means such that upon triggering by the control means, the pump means causes the balloon interior of the peri-aortic jacket to expand and compress the blood vessel, thereby effecting counterpulsation. The pump means may for example pump a gas or liquid (such as sterile water, saline or other suitable fluid with viscosity characteristics 1 Pas to $10^3$ Pas) into the interior of the peri-aortic jacket.

The pump means may, for example, be controlled such that the expansion of the balloon interior of the peri-aortic jacket is subsequently followed by a shrinking (e.g. a relaxation, restoration or correction to the original form) of the balloon interior to effect expansion of the blood vessel.

Alternatively, the actuator means may apply a pressure upon only a part of the blood vessel upon triggering by the control means, compression being effected by the blood vessel being attached to a solid support (or adjacent structure) against which the actuator means applies pressure. For example the vessel may be the descending aorta which compresses against the rigid support of the spine (i.e. a vertebra) the actuator applying pressure to the aorta which compresses against the rigid support for the spine.

The control means may comprise a pacemaker device (for example one manufactured by Medtronics, Pacesetter, Telectronics or Vitatron) attached to the heart by sensor means and configured such that upon diastole the actuator means is triggered and diastolic counterpulsation effected.

The actuator means may be readily attached to the blood vessel, for example a peri-aortic jacket may have a relatively rigid exterior which is hinged or sprung such that one face of the exterior may be opened and the jacket placed around the blood vessel and the exterior face closed. Thus a partial opening can be produced and the jacket can be placed around the blood vessel and then subsequently closed and secured using a clip closure, ratcheted circumferential tie, or other suitable means i.e. surgical wire to secure the closure of the peri-aortic jacket In the case of actuator means applying pressure against the descending aorta attached to the spine a jacket may be attached to the spine, for example by means of stitching or other means, such that the actuator may compress the blood vessel, for example, by means of an expandable balloon (or bladder) or other direct mechanical means.

The use of devices according to the present invention requires a minimally invasive surgical procedure since they do not reside within blood vessels nor require complex surgery or muscular conditioning[6] and thus cause minimal mechanical damage and trauma to blood vessels. Due to their purely mechanical nature they provide an immediate therapeutic benefit and therefore may be used with a wide range of patients for example (but not exclusively) Grade III and IV NYHA patient, particularly those with end-stage failure in functional grades III and IV, together with unstable angina patients who are not suitable for routine bypass surgery.

According to one aspect of the present invention, there is provided a blood circulation assistance device, for location around a blood conduit, the device comprising:

compression means moveable between a contracted form and an expanded form, for compressing the blood conduit to provide counterpulsation;

mechanical driving means, associated with the compression means, for moving the compression means from the contracted form to the expanded form;

control means in communication with the mechanical driving means, the control means being capable of monitoring the cardiac cycle of an individual and triggering the mechanical driving means to move the compression means to the expanded form at diastole; and an outer cuff, surrounding at least a portion of the compression means, providing an outer limiting extent to the movement of the compression means, the compression means being locatable between the blood conduit and the outer cuff such that, in its expanded form, the compression means presses against the outer limiting extent of the outer cuff to compress the blood conduit.

According to another aspect of the present invention, there is provided a blood circulation assistance device comprising:

a compression means, moveable between an expanded and a contracted form; mechanical driving means, associated with the compression means, for moving the compression means from the contracted form to the expanded form; and an outer cuff surrounding at least a portion of the compression means and providing an outer limiting extent to the movement of the compression means, the device being for use in a method of providing counterpulsation to the blood circulation of an individual comprising the steps of:

locating the outer cuff about a blood conduit in the individual, the compression means being between the blood conduit and the outer cuff;

monitoring the cardiac cycle of the individual; and effecting counterpulsation on the blood conduit by operating the mechanical driving means to move the compression means from the contracted form to the expanded form at diastole, the compression means thus pressing against the outer limiting extent of the outer cuff and compressing the blood conduit.

Conveniently the compression means comprises at least one inflatable bladder.

Preferably the mechanical driving means comprises a pump in fluid communication with the at least one inflatable bladder, a fluid being provided in the pump and the at least one inflatable bladder.

Advantageously the pump is connected in fluid communication with the at least one inflatable bladder by a substantially rigid tube.

Conveniently the substantially rigid tube is less than 20 mm long.

Alternatively the pump is located adjacent the at least one inflatable bladder such that the pump is directly connected to the at least one inflatable bladder.

Advantageously the fluid is a liquid, preferably having a viscosity of up to $10^3$ Pas, more preferably from 1 Pas to $10^3$ Pas.

Conveniently the pump comprises a centrifugal impeller rotatable about an axis to effect pumping.

Preferably the impeller is moveable axially between first and second positions to effect a reversal of the direction of pumping.

Advantageously the pump further comprises first and second diffusers for receiving fluid from the impeller, the centrifugal impeller being axially moveable relative to the diffusers between a first position in which the impeller is in fluid communication with the first diffuser and a second position in which the impeller is in fluid communication with the second diffuser to effect a reversal of the direction of pumping.

Conveniently the pump further comprises first and second intakes for supplying fluid to the impeller, the intakes being located such that, in the first position, the centrifugal impeller is in fluid communication with the first intake and in the second position, the impeller is in fluid communication with the second intake.

Conveniently the pump further comprises an electromagnet for sliding the impeller between the first and second positions.

Preferably the pump is an Affeld pump such as is described in U.S. Pat. No. 5,346,458.

Advantageously the compression means comprises a plurality of inflatable bladders.

Conveniently the inflatable bladders are configured to be locatable symmetrically about the axis of the blood conduit.

Preferably the at least one inflatable bladder is made from a material having a tensile strength of from 15 to 35 MPa, preferably 20 to 30 MPa and more preferably 25 MPa.

Advantageously the at least one inflatable bladder is made from a material having a Modulus at 100% elongation of from 2 to 6 MPa, preferably 2.5 to 5 MPa, more preferably 2.64 MPa.

Conveniently the at least one inflatable bladder is made from a material having a modulus at 300% elongation of from 4 to 10 MPa, preferably 6 to 7 MPa, more preferably 6.23 MPa.

Preferably the device further comprises at least one plate connected to the compression means, the at least one plate being locatable adjacent the blood conduit such that when the compression means is in its expanded form the at least one plate compresses the blood conduit.

Advantageously the device comprises two opposing plates, locatable on either side of the blood conduit.

Conveniently the compression means and the mechanical driving means comprise a solid state compression means.

Advantageously the solid state compression means comprises at least one piezoelectric and/or electrostrictive compression elements.

Preferably the solid state compression means comprises an array of compression elements moveable from the contracted to the expanded form.

Conveniently the compression elements in the array are moveable to the expanded form sequentially so as to effect peristaltic compression of the blood conduit.

Preferably the outer cuff has a substantially circular cross-section and is locatable to surround the whole circumference of the blood conduit.

Advantageously the outer cuff is a substantially rigid shell.

Conveniently the outer extent of the outer cuff defines a plane, the outer cuff comprising two portions connected by a hinge perpendicular to the plane such that the outer cuff is moveable from an open configuration for positioning of the device about a blood conduit to a closed configuration for the device to effect counterpulsation of the blood conduit.

Preferably the outer cuff further comprises a clip for locking the two portions of the outer cuff in the closed configuration.

Advantageously the cross section of the outer cuff has an incomplete perimeter bounded by two opposing outer edges along the length of the cuff such that the device is locatable to surround a portion of the circumference of the blood conduit.

Conveniently the device further comprises a substantially rigid panel attachable to the opposing outer edges of the outer cuff such that the rigid panel co-operates with the outer cuff to define the outer limiting extent to the movement of the compression means.

Preferably the opposing outer edges of the outer cuff are attachable to a bone such that the bone co-operates with the outer cuff to define the outer limiting extent to the movement of the compression means.

Advantageously the device further comprises a cushion locatable between the blood conduit and the compression means for cushioning the blood conduit when the compression means moves to the expanded form.

Conveniently the cushion comprises a Teflon™ (known generically as polytetrafluoroethylene (PTFE)) pad.

Preferably the compression means is operable to move from the contracted form to the expanded form in 10 to 200 ms, to remain in the expanded form for between 1 and 300 ms and to return to the contracted form in 10 to 400 ms in order to effect counterpulsation.

Advantageously the device is capable of displacing up to 80 ml of blood from the blood conduit when the compression means moves from the contracted form to the expanded form about a blood conduit, preferably between 15 ml and 40 ml of blood.

Conveniently the blood conduit is an artificial blood conduit.

Preferably the artificial blood conduit is a vascular shunt.

Advantageously the diameter of the vascular shunt tapers from one end of the shunt to the other end.

Conveniently the artificial blood conduit is integral to the blood circulation assistance device.

Preferably the control means comprise a pacemaker.

Alternatively the pump means is powered electrically, the control means comprising means for monitoring the current to the pump means.

Advantageously the device does not comprise means to effect copulsation.

According to another aspect of the present invention there is provided a method of providing counterpulsation to the blood circulation of an individual comprising the steps of:

providing a blood circulation assistance device comprising: compression means, moveable between an expanded and a contracted form; mechanical driving means, associated with the compression means, for moving the compression means from the contracted form to the expanded form; and an outer cuff, surrounding at least a portion of the compression means, and providing an outer limiting extent to the movement of the compression means;

locating the outer cuff about a blood conduit in the individual, the compression means being between the blood conduit and the outer cuff;

monitoring the cardiac cycle of the individual; and effecting counterpulsation on the blood conduit by operating the mechanical driving means to move the compression means from the contracted form to the expanded form at diastole, the compression means thus pressing against the outer limiting extent of the outer cuff and compressing the blood conduit.

Conveniently the method uses the blood circulation assistance device described above.

Preferably the step of locating the outer cuff about the blood conduit comprises:

moving the outer cuff into the open configuration;

positioning the outer cuff about the blood conduit; and moving the outer cuff into the closed configuration.

Advantageously the step of locating the outer cuff about the blood conduit further comprises the step of, after moving the outer cuff into the closed configuration:

locking the two portions of the outer cuff with the clip.

Preferably the step of locating the outer cuff about the blood conduit comprises:

inserting the blood conduit through the opposing outer edges of the outer cuff; and attaching the substantially rigid panel to the opposing outer edges of the outer cuff so that the whole circumference of the blood conduit is surrounded by the outer limiting extent defined by the outer cuff and the substantially rigid panel.

Advantageously the step of locating the outer cuff about the blood conduit comprises:

inserting the blood conduit through the opposing outer edges of the outer cuff; and attaching the opposing outer edges of the outer cuff to a bone in the individual so that the whole circumference of the blood conduit is surrounded by the outer limiting extent defined by the outer cuff and the bone.

Conveniently the bone is a vertebra.

In an alternative, the method further comprises the steps of severing a blood vessel in the individual to provide two ends of the blood vessel and attaching either end of the artificial blood conduit to a respective end of the blood vessel.

Advantageously the method further comprises the step of removing a section of the blood vessel prior to attaching either end of the artificial blood conduit to the respective ends of the blood vessel.

Conveniently the method further comprises the steps of grafting either end of the vascular shunt to a blood vessel in the individual such that blood passes through the vascular shunt in parallel with the blood vessel.

Preferably the blood conduit is a blood vessel in the individual.

Conveniently the method further comprises the step of inserting a synthetic patch into the wall of the blood vessel to increase the diameter of the blood vessel.

Advantageously the blood vessel is the aorta of the individual.

Conveniently the blood vessel is the ascending aorta.

Preferably the blood vessel is the descending aorta.

Advantageously no copulsation is performed.

According to a further aspect of the present invention there is provided the use of a pump means for effecting counterpulsation on an individual, wherein the pump means comprises a centrifugal impeller rotatable about an axis to effect pumping, the impeller being moveable axially between first and second positions to effect a reversal of the direction of pumping.

In this specification, the word "comprising" means "including" or "consisting of" and the word "comprises" means "includes" or "consists of".

In this specification, "mechanical" means apparatus that is mechanical, electromechanical (including solid-state electromechanical), or a hydraulic apparatus with mechanical components .

In this specification, "blood conduit" means a natural blood vessel; a synthetic or artificial blood vessel; or other tubular structure for carrying blood.

The invention will be further apparent from the following description, with reference to the accompanying drawings, which show, by way of example only, embodiments or parts of embodiments of blood circulation assistance devices, wherein.

Figure 1:
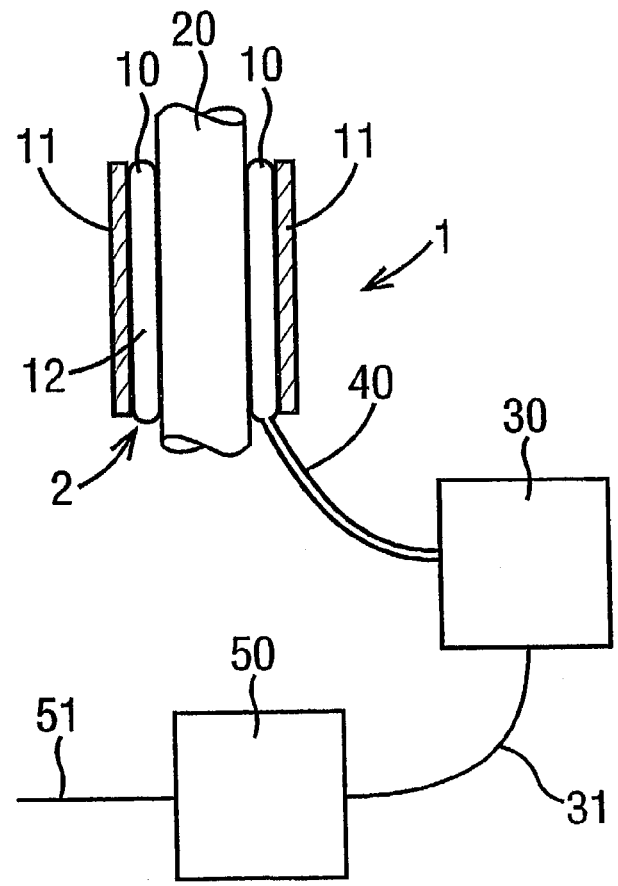
FIG. 1 is a part longitudinal cross-sectional, part schematic view of a blood circulation assistance device according to one embodiment of the present invention.

Referring to FIG. 1, a blood circulation assistance device 1, in particular, an extravascular counterpulsator device, according to one embodiment of the present invention is provided. The blood circulation assistance device 1 comprises an actuator means 2 comprising a peri-aortic jacket 10,11. The peri-aortic jacket 10, 11 comprises an expandable or inflatable balloon or bladder interior 10 and a relatively rigid hinged exterior cuff 11. The inflatable bladder 10 is of annular cross-section and is located about the outer circumference of the ascending aorta 20 of an individual. The inflatable bladder 10 extends parallel to the longitudinal axis of the aorta 20. The inflatable bladder 10 is filled with a fluid 12 and is moveable between a contracted form (shown in FIG. 1) in which the fluid 12 is of relatively low pressure and an expanded form in which the fluid 12 is of relatively high pressure. The fluid is a liquid or a gas. In the embodiments in which the fluid 12 is a liquid, it may be a mineral oil, water or the like. The viscosity of the fluid is up to $10^3$ Pas, preferably between 1 and $10^3$ Pas. The viscosity of the fluid 12 can be increased, if required, by the addition of polysaccharides.

The cuff 11 is also of annular cross-section and is located about the outer circumference of the bladder 10, extending parallel to the longitudinal axis of the aorta 20. Consequently, the inflatable bladder 10 and the cuff 11 are substantially cylindrical and coaxially surround the aorta 20. Furthermore, the inner circumference of the relatively rigid cuff 11 defines an outer extent to the movement of the inflatable bladder 10, the inflatable bladder being unable to move outwardly of the outer extent even when in the expanded form.

The actuator means 2 also comprises pump means 30 attached (i.e. connected) to the interior of the bladder 10 of the peri-aortic jacket by a connecting tube 40. Thus the pump means 30 are in fluid communication with the interior of the bladder 10. The pump means 30 are attached by a lead 31 to pacemaker control means 50,51. The pacemaker control means comprises a pacemaker 50 and a sensor 51, the pacemaker being configured (i.e. programmed) to trigger at diastole so as to effect aortic counterpulsation of the blood vessel 20, the sensor 51 being attached to the heart cardiac tissues (not illustrated) in order to monitor the cardiac cycle.

In use, the peri-aortic jacket is placed around the ascending aorta 20 such that the bladder 10 and the cuff 11 surround the whole circumference of the aorta 20. The other components of the blood circulation assistance device are located in suitable positions within the body of the individual which positions will differ from person to person. The sensor 51 monitors the cardiac cycle of the individual and communicates this information to the pacemaker 50. At diastole in the cardiac cycle, the pacemaker 50 sends a signal to the pump means 30. In response to the signal, the pump means 30 pumps the fluid 12 through the connecting tube 40 and into the inflatable bladder 10 thus increasing the pressure of the fluid 12 in the inflatable bladder 11. Consequently, the inflatable bladder moves from its contracted form to its expanded form. The interior circumference of the cuff 11 defines an outer limiting extent beyond which the inflatable bladder 10 cannot expand. Because of this outer limiting extent, the bladder 10 presses against the interior of the cuff 11 and expands inwardly, thus compressing the aorta 20. In some embodiments the aorta 20 is completely occluded by the compression whereas in other embodiments, the aorta 20 is only partially occluded.

After a predetermined period of time, but also during diastole, the pacemaker 50 sends a further signal to the pump means 30. In response to this further signal, the pump means 30 pumps the fluid 12 through the connecting tube 40 out of the inflatable bladder 10. This decreases the pressure of the fluid 12 in the inflatable bladder 10 and the bladder moves from its expanded form to its contracted form. Because of the inherent resilience of the aorta 20, the aorta returns to its initial form, after having been compressed, as the bladder 10 returns to its contracted form.

The sensor 51 continues to monitor the cardiac cycle of the individual and, at diastole, the above described process is repeated.

In some embodiments, the pump means 30 do not actively pump the fluid 12 out of the inflatable bladder 10 when the bladder 10 returns to the contracted form. In these embodiments, the inherent internal pressure of the aorta 20 automatically returns the bladder 10 to the contracted form once the pump means 30 ceases to pump the fluid 12 into the bladder 10.

Figure 2:
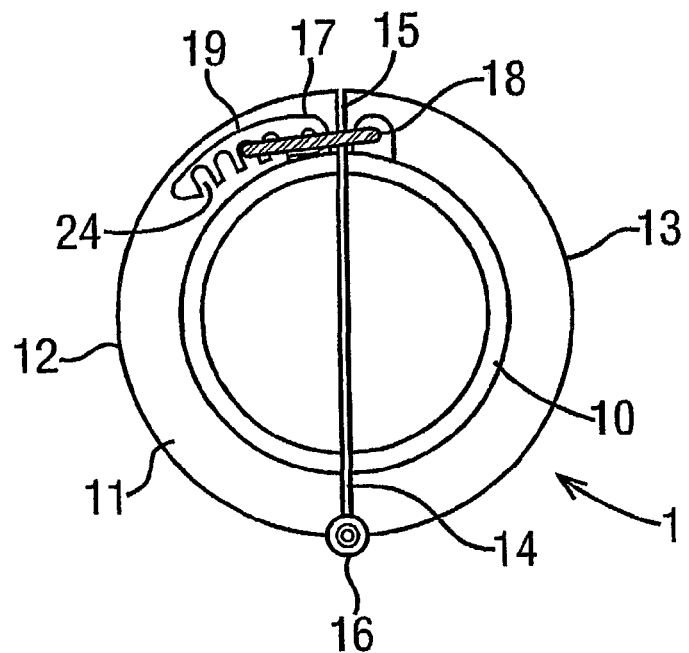
FIG. 2 is a radial cross-sectional view of a blood circulation assistance device, in a first state, according to another embodiment of the present invention.
Figure 3:
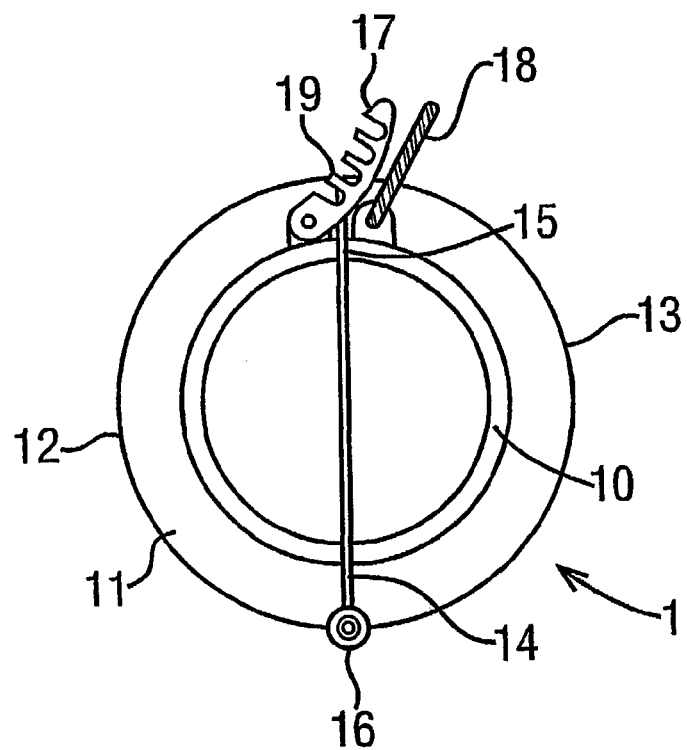
FIG. 3 is a radial cross-sectional view of the blood circulation assistance device of FIG. 2 in a second state.

Referring to FIGS. 2 and 3, another embodiment of blood circulation assistance device 1 is shown. As in the previous embodiment, the blood circulation assistance device 1 comprises an inflatable bladder 10 of annular cross-section surrounded by a cuff 11 also of annular cross-section. In this embodiment the inflatable bladder 10 and the cuff 11 each comprise first and second sections 12, 13 separated by first and second longitudinal breaks 14, 15. Thus, in fact, each of the first and second sections 12, 13 of the inflatable bladder 10 and the cuff 11 comprise a section having a semi-circular cross-section.

The first and second sections 12, 13 are connected by a hinge 16 attached to either edge of the first and second sections of the cuff 11 adjacent the first longitudinal break 14. A releasable clip 17 is provided adjacent the second longitudinal break 15. The releasable clip 17 comprises a loop 18, one end of which is rotatably attached to the edge of the second section 13 of the cuff 11 adjacent the second longitudinal break 15. The releasable clip 17 also comprises a catch 19, one end of which is rotatably attached to the edge of the first section 12 of the cuff 11 adjacent the second longitudinal break 15. The catch 19 is provided with a series of lugs 24 in which the other end of the loop 18 may be engaged.

In this embodiment, an additional pipe (not shown) is provided to connect the first and second sections of the bladder 10 in order to ensure that the two sections are in fluid communication with one another and can be pressurised.

In use of this embodiment, the clip 17 is released by rotating the catch 19 away from the cuff 11 and rotating the loop 18 so that it is no longer engaged in any of the lugs 24. The clip is then in the released state shown in FIG. 3. The first and second sections 12, 13 of the bladder 10 and the cuff 11 are then swung apart about the hinge 16. The blood circulation assistance device 1 is then placed around a blood vessel in an individual and the first and second sections 12, 13 are swung back together to surround the blood vessel. The clip 17 is then secured by rotating the loop 18 over the catch 19 so that the loop 18 engages in one of the lugs 24 and then rotating the catch 19 towards the cuff 11 to tension the loop 18. The clip is then in the closed state shown in FIG. 2. Counterpulsation of the blood vessel is then effected as has been described in relation to the previous embodiment.

The advantage of such embodiments of the invention are that the blood vessel does not need to be severed in order locate the blood circulation assistance device 1 surrounding the blood vessel.

In some other embodiments, the bladder 10 and cuff 11 are also split into first and second sections 12, 13 to allow the blood circulation assistance device 1 to be located around a blood vessel. However, in these embodiments, other means are provided to secure the two sections in the closed state. For example, in some embodiments of the invention, a circumferential tie such as a nylon band, or surgical wire are used instead of the clip 17.

Figure 4:
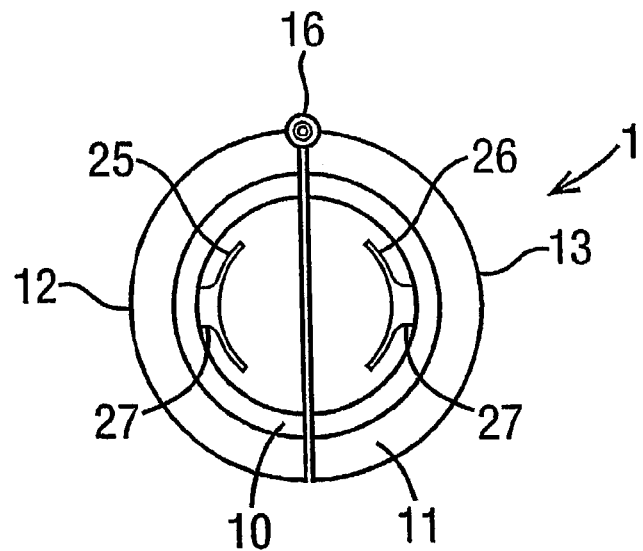
FIG. 4 is a radial cross-sectional view of a blood circulation assistance device in accordance with another embodiment of the present invention.

With reference to FIG. 4, another embodiment of the present invention is shown. The blood circulation assistance device 1 comprises an inflatable bladder 10 of annular cross-section surrounded by a cuff 11 also of annular cross-section, as in the previous embodiments. As in the previous embodiment, the bladder 10 and cuff 11 are split into first and second sections 12, 13, connected by a longitudinal hinge 16. In this embodiment, first and second plates 25, 26 are provided, attached to the inner circumference of the bladder 10. The plates 25, 26 are located opposing each other, each one in the centre of one of the semi-circular cross-sections of the first and second sections 12, 13. The first and second plates 25, 26 are arcuate, the arc being coaxial with the cross-sections of the bladder 10 and cuff 11 and are each connected to their respective section of the bladder 10 by a short stem 27.

In use of this embodiment, the blood circulation assistance device 1 is located around a blood vessel as described in relation to the previous embodiment. However, in this embodiment, the inner circumference of the bladder 10 is slightly smaller than the outer circumference of the blood vessel that the device surrounds. Thus the bladder 10 does not contact the blood vessel directly. Instead, the first and second plates 25, 26 project inwardly so as to grip the exterior of the blood vessel. The blood vessel thus sits between the arcuate first and second plates 25, 26. When the bladder 10 is moved into its expanded form, the first and second plates 25, 26 are pushed inwardly by the bladder 10 so as to compress the blood vessel. In other respects, the working of this embodiment of the invention is similar to the previously described embodiments.

In some alternative embodiments, the bladder 10 does not have an annular cross-section. For example, in some embodiments, the bladder 10 is elongate and is wrapped helically around the blood conduit before the outer cuff is secured around the bladder 10.

Figure 5:
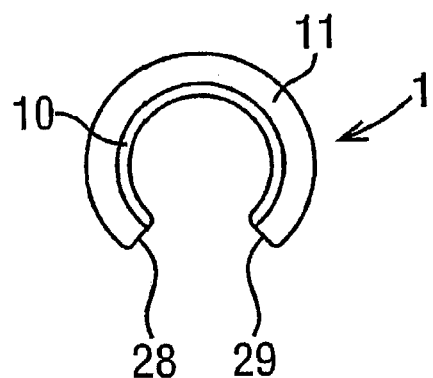
FIG. 5 is a radial cross-sectional view of a blood circulation assistance device in accordance with another embodiment of the present invention.

Referring to FIG. 5, a further embodiment of the present invention is shown. In this embodiment, the blood circulation assistance device 1 comprises an inflatable bladder 10 surrounded by a cuff 11. However, in this embodiment, the bladder 10 and the cuff 11 are not of annular cross-section. Instead, the bladder 10 and the cuff 11 have a cross-section having the shape of around 270° of arc of a circle. Thus the cross-section of the bladder 10 and the cuff 11 has an incomplete perimeter, comprising only around three-quarters of a circle. The incomplete section of the perimeter is bounded by two opposing edges 28, 29 which extend along the length of the blood circulation assistance device 1.

In use of this embodiment, the blood circulation assistance device 1 is located surrounding a blood vessel by sliding the blood vessel through the incomplete section of the bladder 10 and cuff 11, between the two opposing edges 28, 29. The blood circulation assistance device 1 is of a size such that the bladder 10, in its contracted form, fits snugly around the blood vessel. Thus there is no requirement for the blood circulation assistance device 1 to be hinged or for there to be additional securing means to hold the blood circulation assistance device 1 in place since it is held in place by friction alone.

Figure 6:
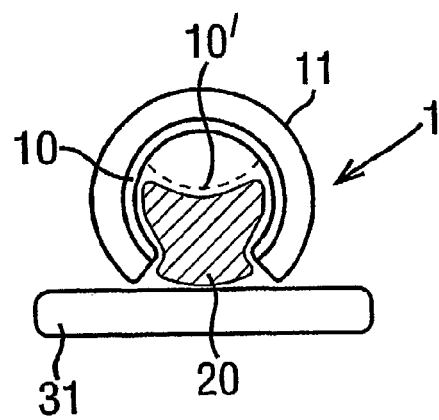
FIG. 6 is a radial cross-sectional view of a blood circulation assistance device in accordance with another embodiment of the present invention, with a dashed line showing a part in an alternative position.

A variation of this embodiment of the invention is shown in FIG. 6. This embodiment is identical to the previous embodiment except that a planar panel 31 is provided, extending between and attached to the two opposing edges 28, 29. The blood vessel 20 is thus surrounded by the inflatable bladder 10 and cuff 11 on one side and the panel 31 on the other side. In FIG. 6, the position of the bladder 10 in the expanded form is shown by the dashed line 10'.

In use of this particular embodiment, the blood vessel 20 is inserted between the two opposing edges 28, 29 of the blood circulation assistance device 1, with the panel 31 removed. The panel 31 is then attached to each of the two opposing edges 28, 29 so as to secure the blood vessel 20 with the blood circulation assistance device 1. The panel 31 is attached to the blood circulation assistance device 1 by means of stitching, suturing, clips staples or other means. Counterpulsation of the blood vessel 20 is then effected as has been described in relation to the other embodiments of the invention, the dashed line showing the position of the bladder 10 in the expanded form. The advantage of this particular embodiment is that it is relatively easy to secure the blood circulation assistance device 1 around a blood vessel without the need to sever the blood vessel. Furthermore, the whole circumference of the blood vessel is surrounded by the blood circulation assistance device 1 so that there is a greater efficiency in the compressing of the blood vessel 20.

Figure 7:
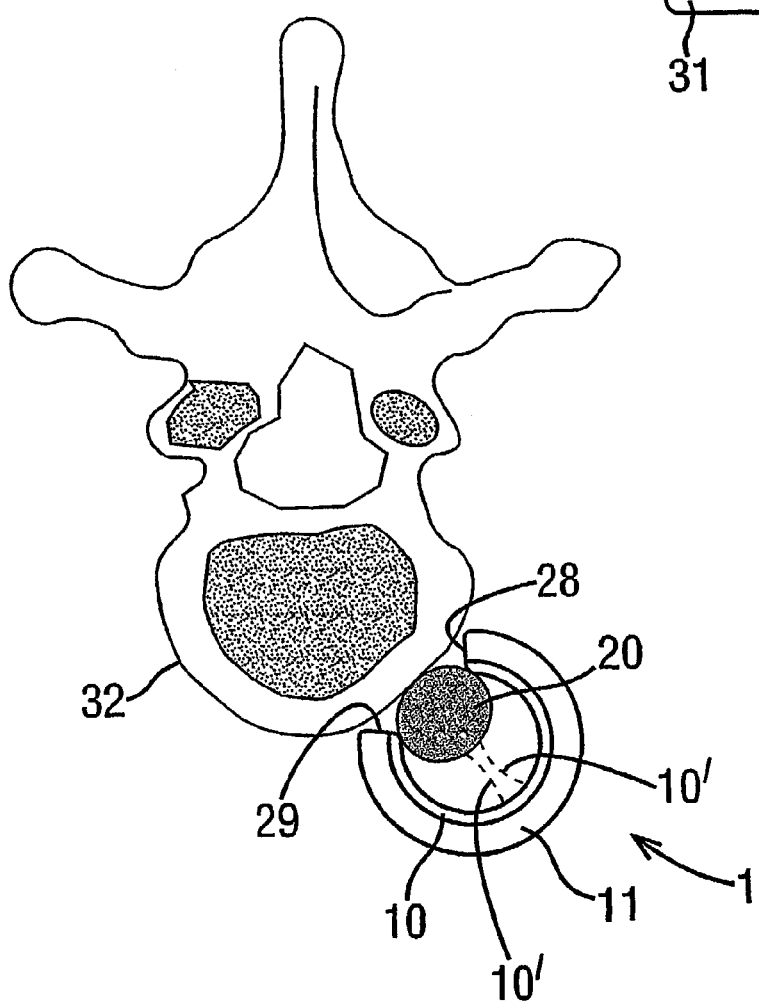
FIG. 7 is a radial cross-sectional view of a blood circulation assistance device in accordance with another embodiment of the present invention and a vertebra, with a dashed line showing a part in an alternative position.

A further variation of the previously described embodiment is shown in FIG. 7. In this embodiment, the blood circulation assistance device 1 is identical to the device of the previous embodiment except that no panel 31 is provided. Furthermore, the blood circulation assistance device 1 comprises two inflatable bladders 10 whose position in the expanded form is shown by the lines 10'. In this embodiment, the blood circulation assistance device 1 is attached to a vertebra 32 at the two opposing edges 28, 29 of the cuff 11. Thus the vertebra 32 co-operates with the cuff 11 to define the outer limiting extent beyond which the bladder 10 may not expand.

In use of this embodiment, the blood vessel 20 is inserted between the two opposing edges 28, 29 of the blood circulation assistance device 1. The two opposing edges 28, 29 of the cuff 11 are then attached to the vertebra 32, by stitching, suturing, clips, staples or other means. Counterpulsation of the blood vessel 20 is then effected as has been described in relation to the other embodiments of the invention, the dashed lines showing the position of the bladder 10 in the expanded form. The vertebra 32 and the cuff 11 co-operate to define an outer limiting extent and restrain the outward expansion of the bladder 10 in order to increase the efficiency of compression on the blood vessel 20.

In some alternative embodiments, the blood circulation assistance device 1 is attached to a thoracic rib of the individual rather than to the vertebra 32.

Figure 8:
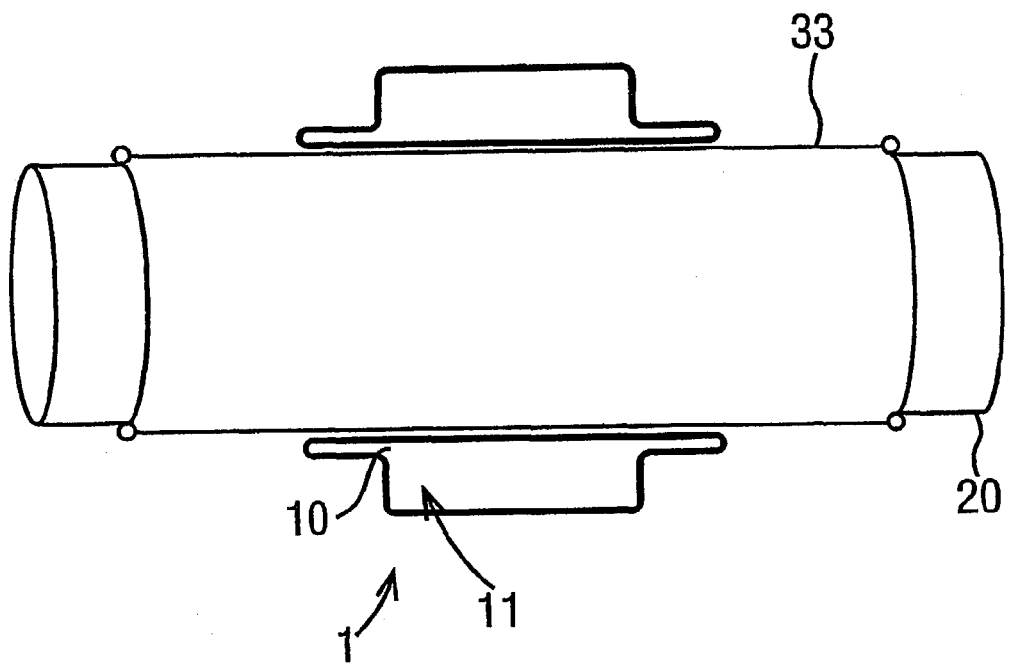
FIG. 8 is side view of a blood circulation assistance device in accordance with another embodiment of the present invention, with part cut away.

Referring now to FIG. 8, a side view of a further embodiment of the present invention is shown, with the bladder 10 and cuff 11 cut away for clarity. In this embodiment, the blood circulation assistance device 1 comprises the coaxially arranged bladder 10 and cuff 11 as described in the previous embodiments. In this embodiment, the blood circulation assistance device 1 additionally comprises a cushion 33 wrapped around the blood vessel 20. Thus the cushion 33 interposes between the bladder 10 and the blood vessel 20 in order to protect the blood vessel 20 under repeated compression. The cushion 33 is a pad made from Teflon™ or Dacron™.

In a variation of this embodiment, instead of the cushion 33, a synthetic patch of, for example, Dacron™ is grafted into the wall of a blood vessel in order to increase the diameter of a section of the blood vessel. The blood circulation assistance device 1 is then located around this section of the blood vessel and counterpulsation is effected in accordance with the previously described embodiments. Because this section of the blood vessel has an increased diameter, it contains an increased volume of blood. Thus when the section of blood vessel is compressed an increased quantity of blood is displaced. Therefore, this procedure enables the blood circulation assistance device 1 to counterpulsate more effectively. Furthermore, the synthetic patch increases the resilience of the blood vessel which increases the effectiveness of counterpulsation in situations where the blood vessel has suffered hardening.

In certain variations of this embodiment, an entire section of a blood vessel is removed and replaced by a synthetic graft. The blood circulation assistance device 1 is then located around the synthetic graft in order to effect counterpulsation. Indeed, in certain embodiments, the blood circulation assistance device 1 is provided with an integral synthetic blood vessel as its innermost layer, which synthetic blood vessel can be grafted into the existing ends of the natural blood vessel. These procedures are particularly useful when the section of natural blood vessel in question is diseased and must, in any case, be removed. In these embodiments, it is not necessary for the bladder 10 and outer cuff 11 to have any means of opening (such as the longitudinal hinge 16 described above) in order to fit over the blood conduit because they are inserted between the ends of a blood vessel. In some embodiments, the synthetic graft has a larger internal diameter than the section of blood vessel that it replaces to increase the volume of blood that is contained in the graft and thus increase the volume of blood displaced by each compression of the blood circulation assistance device 1.

In some embodiments of the invention, the outer cuff 11 comprises a plurality of separate cuff pieces. In some versions of these embodiments the cuff pieces are connected in series by interposing articulated sections. Thus the outer cuff 11 can be shaped so as not to follow a single straight line but a curve or series of curves. This allows the blood circulation assistance device 1 to be located on blood conduits which have a substantial curve and thus allows relatively large devices, able to displace large volumes of blood, to be implanted.

Indeed, in some embodiments, no articulated sections are required because the entire outer cuff 11 is preformed as a shaped unit to fit a particular section of the aorta 20. This is achieved, in some embodiments, by having a range of preformed outer cuffs 11 of differing sizes and shapes, one of which is selected because it fits the blood vessel of a particular individual. In other embodiments, measurement of the individual's blood vessel are made pre-operatively, and a shaped outer cuff 11 is manufactured (for example, using a computer-numerically-controlled milling machine) specifically to fit around the blood vessel. Thus, in these embodiments, the outer cuff 11 is uniquely fitted for the blood vessel of the individual.

In other versions, there is no direct connection between the cuff pieces. In use, the bladder 10 is placed around the blood conduit and a series of cuff pieces are placed around the blood conduit and the bladder 10 in accordance with any of the procedures described above. Thus a series of sections of the bladder 10 are surrounded by a respective cuff piece. Although the efficiency of compression of the blood conduit is reduced in sections which are not surrounded by a cuff piece, the overall effect of the cuff pieces is sufficient to enable effective compression of the blood conduit and counterpulsation to take place.

Figure 9:
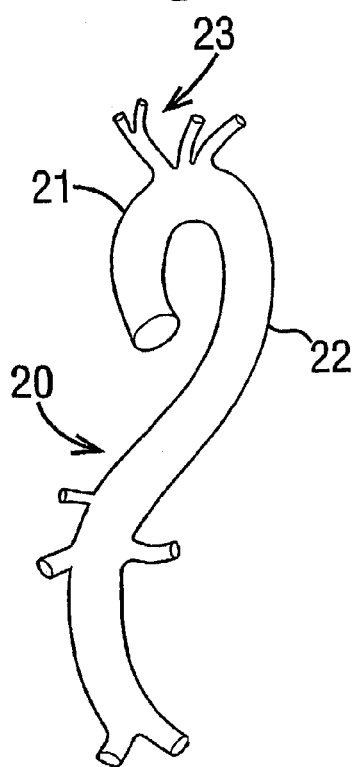
FIG. 9 is a side view of an aorta.
Figure 10:
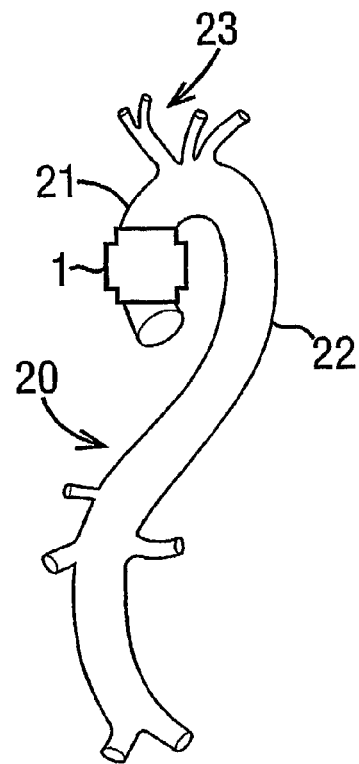
FIG. 10 is a side view of a blood circulation assistance device according to one embodiment of the present invention located on an aorta.
Figure 11:
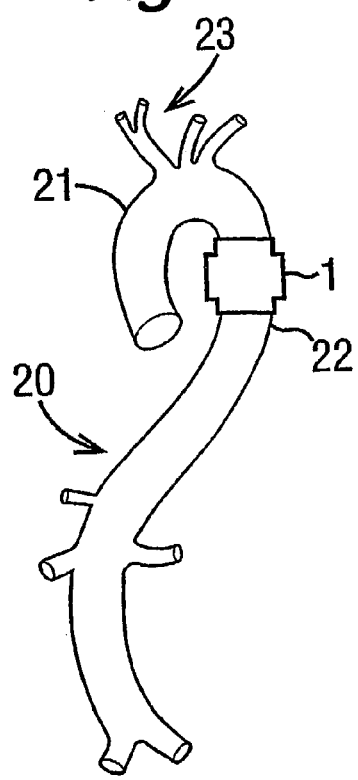
FIG. 11 is a side view of a blood circulation assistance device according to one embodiment of the present invention in another location on an aorta.

Referring now to FIGS. 9, 10 and 11, the location of the blood circulation assistance device 1, in certain embodiments of the invention will be described. The aorta 20 comprises the ascending aorta 21 which leads from the heart (not shown) and the descending aorta 22 leading towards the rest of the body.

Referring to FIG. 10, in some embodiments of the present invention, the blood circulation assistance device 1 is located surrounding the ascending aorta 21. The advantage of locating the blood circulation assistance device 1 surrounding the ascending aorta 21 is that the device 1 is located relatively closely to the heart and it has been found that only a relatively small displacement of blood (such as 20 ml) is required in order to achieve effective counterpulsation in this location. In addition, when the blood circulation assistance device 1 is located surrounding the ascending aorta 21, it is downstream of the blood vessels 23 which lead to the brain. Therefore when the blood circulation assistance device 1 is located in this position it is more effective at increasing the supply of blood to the brain. Because the ascending aorta 21 is relatively short, it is necessary for the blood circulation assistance device 1 to be around 20 to 40 mm long in order that it fits around the ascending aorta.

In some other embodiments of the invention, shown in FIG. 11, the blood circulation assistance device 1 is located surrounding the descending aorta 22. Because the descending aorta is longer than the ascending aorta 21, it is possible for the blood circulation assistance device 1 to be longer, e.g. up to 60 mm long. Furthermore, calcification of the aorta may occur if the blood circulation assistance device 1 is located surrounding the ascending aorta 21 which is avoided if the blood circulation assistance device 1 is located surrounding the descending aorta 22.

Figure 12:
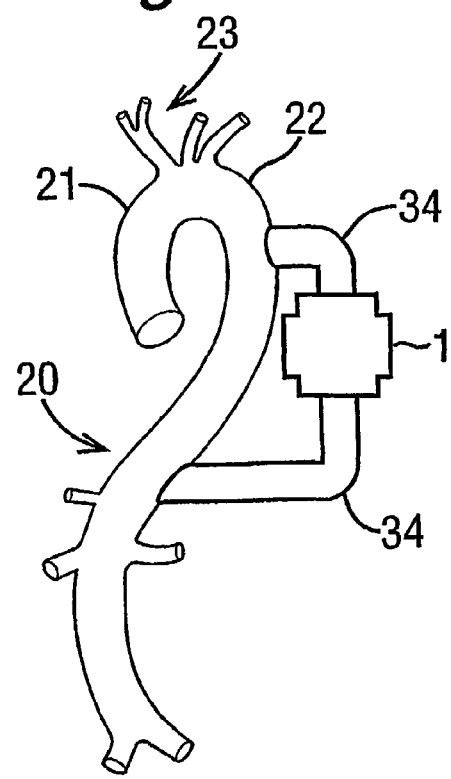
FIG. 12 is a side view of a blood circulation assistance device according to another embodiment of the present invention.

A side view of a further embodiment of the present invention is shown in FIG. 12. In this embodiment, a vascular shunt 34 is provided on the descending aorta 22. The vascular shunt 34 comprises a hollow tube made from, for example, polyurethane or Dacron™, either end of which is grafted onto the wall of the descending aorta 22, one end distal to the other. An aperture in the wall of the descending aorta 22 is provided beneath each graft so that blood passing through the aorta 20 passes not only through the descending aorta 22 but also through the vascular shunt 34. Accordingly the blood flows through the aorta 20 in parallel with the blood following through the vascular shunt 34.

In this embodiment, the blood circulation assistance device 1 is located around the vascular shunt 34. Thus, in this embodiment, the blood circulation assistance device 1 is not located around a blood vessel but is instead located around another blood conduit, namely the synthetic vascular shunt 34. The blood circulation assistance device 1, itself, is substantially the same as in the previous embodiments.

In use, this embodiment operates in a similar manner to the previously described embodiments. Therefore, in response to signals concerning the cardiac rhythm of the individual, the bladder 10 is moved from its contracted to its expanded form at diastole, pressing against the outer cuff 11 and compressing the vascular shunt 34. This effects counterpulsation by forcing blood out of the vascular shunt 34.

The advantage of this particular embodiment is that the vascular shunt 34 can be made considerably longer than any one section of the aorta 20. This allows for easier access to the blood conduit when the blood circulation assistance device 1 is fitted and allows for the blood circulation assistance device 1, itself, to be longer and so displace more blood at each compression. Thus, in some versions of this embodiment, the blood circulation assistance device 1 is long enough to displace up to 80 ml of blood when the vascular shunt 34 is compressed.

A further advantage of this embodiment is that the blood circulation assistance device 1 can be located about the vascular shunt 34 outside the body under straightforward conditions and then the combination of vascular shunt 34 and blood circulation assistance device 1 is implanted into an individual simultaneously. Indeed, in certain embodiments, the blood circulation assistance device 1 and vascular shunt 34 are formed as an integral unit.

In some further variations of this embodiment, the vascular shunt 34 has an interior diameter that tapers from one end to the other. In some embodiments, the distal end of the vascular shunt 34 has a narrower diameter than the proximal end but in other embodiments the proximal end of the vascular shunt 34 has a narrower diameter than the distal end. The effect of the tapering of the diameter is that blood is preferentially expelled from the end of the vascular shunt 34 with the wider diameter when the vascular shunt 34 is compressed. This can be useful when it is desired to increase the supply of blood to a particular part of the circulation adjacent to the wider end of the vascular shunt 34.

Figure 13:
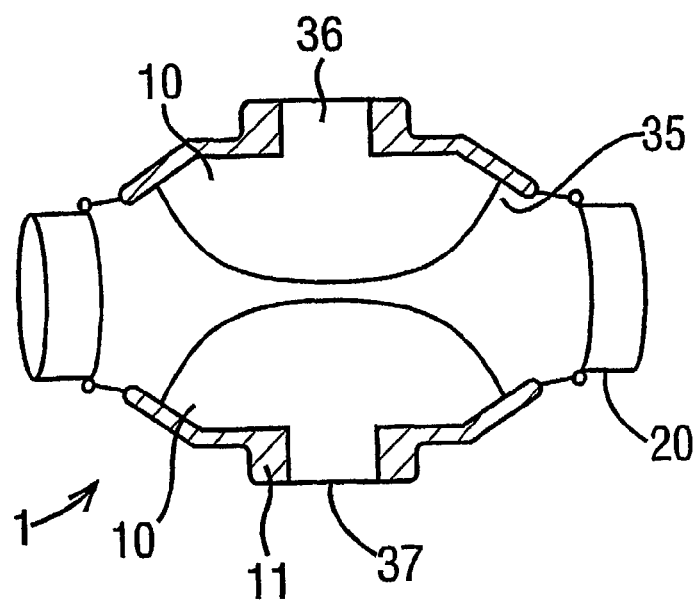
FIG. 13 is a longitudinal cross-sectional view of a further embodiment of the present invention.

Referring now to FIG. 13, a longitudinal cross-sectional view of a blood circulation assistance device 1 in accordance with a further embodiment of the invention is shown. The blood circulation assistance device 1 comprises an outer cuff 11 being generally tubular in form and having a central longitudinal lumen 35 through which a blood vessel 20, or other blood conduit, may extend. The lumen 35 is narrowest at either end of the cuff 11, being of approximately the same diameter as the outer diameter of the blood conduit which it surrounds, thus gripping the blood conduit 20. The inner section of the lumen is recessed such that the lumen is widest at the centre of the cuff 11. On two opposing sides of the cuff 11, at the broadest section of the lumen 35, are provided apertures 36, 37, leading to the pump means 30. In some embodiments, the apertures 36, 37 lead to the pump means 30 via a connecting tube 40 that bifurcates from the pump means 30 to connect separately to the two apertures 36, 37. In other embodiments, no connecting tube 40 is provided and the two apertures 36, 37 connect directly to the pump means 30.

An inflatable bladder 10 is provided over each of the two apertures 36, 37, on the interior of the cuff 11 such that each bladder is in fluid communication with the pump via its respective aperture 36, 37. Each bladder 10 is moveable between a contracted form when its internal pressure is relatively low and in which each bladder 10 resides within the recessed section of the lumen 35 and an expanded form (as is shown in FIG. 13) when the internal pressure is relatively high and in which each bladder extends into the central lumen of the cuff 11, thus compressing the blood vessel 20.

In use, the pump means 30 drives fluid through the apertures 36, 37 at diastole in order to increase the pressure within the two bladders 10 and move them from their contracted form to their expanded form in order to compress the blood conduit 20. Subsequently, the pump drives fluid out from the two bladders 10, through the apertures 36, 37 to move the bladders 10 from their expanded form to their contracted form thus releasing the compression on the blood conduit 20. In this way, counterpulsation is effected.

It is to be appreciated that, in this embodiment of the invention, two bladders 10 are provided, on opposing sides of the blood conduit 20 that they surround. In alternative embodiments of the invention, more than two bladders 10 are provided. In particular embodiments, three, four, five or even more bladders 10 are provided around the blood conduit 20. It is preferred, however, when a plurality of bladders 10 are provided, that the bladders are spaced equidistantly around the blood conduit 20 so that the bladders are symmetric about the longitudinal axis of the blood conduit 20.

In embodiments of this invention, the inflatable bladder or bladders 10 are fabricated using a flexible, fatigue resistant material suitable for implant applications. In some embodiments, the material is resilient. For example a flexible polymer film such as poly ethethylene terephthalate (PET) is used in some embodiments or resilient classes of polymer such as a linear polyurethanes, silicones or thermoplastic elastomers are used in other embodiments. It is preferred that the material has the following range of material properties. The tensile strength is between 15 and 35 MPa, preferably 20 to 30 MPa more preferably 25 MPa. The Modulus at 100% elongation is between 2 and 6 MPa, preferably 2.5 to 5 MPa, more preferably 2.64 MPa. The Modulus at 300% elongation is between 4 and 10 MPa, preferably between 6 and 7 MPa, more preferably 6.23 MPa.

In some embodiments, the inflatable bladder or bladders 10 are made from a braided structure or fabric to restrict strain and control when in the expanded form.

Suitable materials which may be selected for the fabrication of the bladder 10 are listed in the following table.

| Material or Chemical class | | Tradename |
|---|---|---|
| poly ethyleneterephthalate | PET | |
| thermoplastic elastomers | TPE's | Santoprone ™ |

| Material or Chemical class | | Tradename |
|---|---|---|
| -continued | | |
| poly urethanes | PEU | Estane ™ |
| silicones | | Silastic ® |
| oriented polyethylene | braided monofilament | Dyneema ™ |

In embodiments of this invention, the outer cuff 11 is fabricated using medical plastics or metallic alloys approved for such use. Preferably, the material has the following properties. The tensile strength is from 70 to 80 MPa, more preferably 76 MPa. The Flexural Modulus is from 2 to 4 GPa, more preferably 2.8 to 3.4 GPa, more preferably 3.1 GPa. Examples of suitable materials are listed in the table below.

| Material or Chemical class | Tradename | |
|---|---|---|
| Titanium cp | Ti | |
| Vitallium | TiAlV6 | Vitallium ™ |
| Polyethylene | UHMWPE, HDPE, PE | |
| Polypropylene | PP | |
| poly ethyleneterephthalate | PET | |
| poly butyleneterephthalate | PBT | |
| poly carbonate | PC | |
| poly ethersulphone | PES | |
| poly etheretherketone | PEEK | Victrex PEEK ™ |
| poly-methyl methacrylate | pMMA | |
| poly phenylsulphone | PPS | |
| poly urethanes | PEU | Bionate ™ |
| | | Corethane ™ |
| | | Pellethane ™ |
| poly amides | PA | Nylon |
| poly oxymethylene | POM | Delrin ™ |
| Polystyrene | PS | |

The properties required for the material from which the cuff 11 is made depend on factors such as its intended location, and the volume of blood it displaces when the blood conduit is compressed. For example, in the ascending aorta, if a thin, radio opaque construction is required then, a medical alloy such as titanium CP is used for fabrication, or alternatively a rigid polymer such as poly etheretherketone (PEEK) containing a radio opacifying agent is used.

In some embodiments of the invention, the outer cuff 11 is not made from a rigid material. In these embodiments the outer cuff 11 is made from a deformable but non-extensible material such as a fabric. In some of these embodiments, the cuff 11 is partly formed in situ, with a length of fabric being stitched around a blood conduit and the bladder 10, in the individual. However, it is particularly important in all of these embodiments that the material be non-extensible such that the cuff 11 is able to define an outer limiting extent beyond which the bladder 10 may not extend such that the expansion of the bladder 10 presses against the cuff 11 to compress the blood conduit more efficiently.

In embodiments of this invention the pump means 30 is a mechanical pump powered from a battery. The battery is connected to a coil, which is also implanted within the individual, just beneath the skin such that the battery can be recharged by locating an external coil adjacent the internal coil and transferring energy between the two coils by induction.

Figure 14:
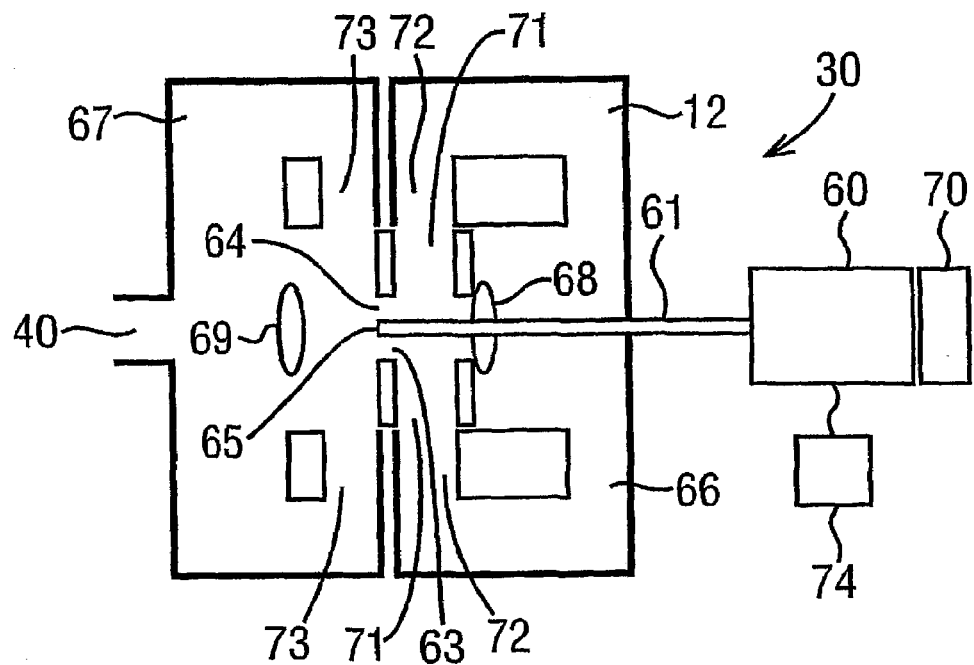
FIG. 14 is a schematic view of a portion of a blood circulation assistance device of one embodiment of the present invention in a first position.
Figure 15:
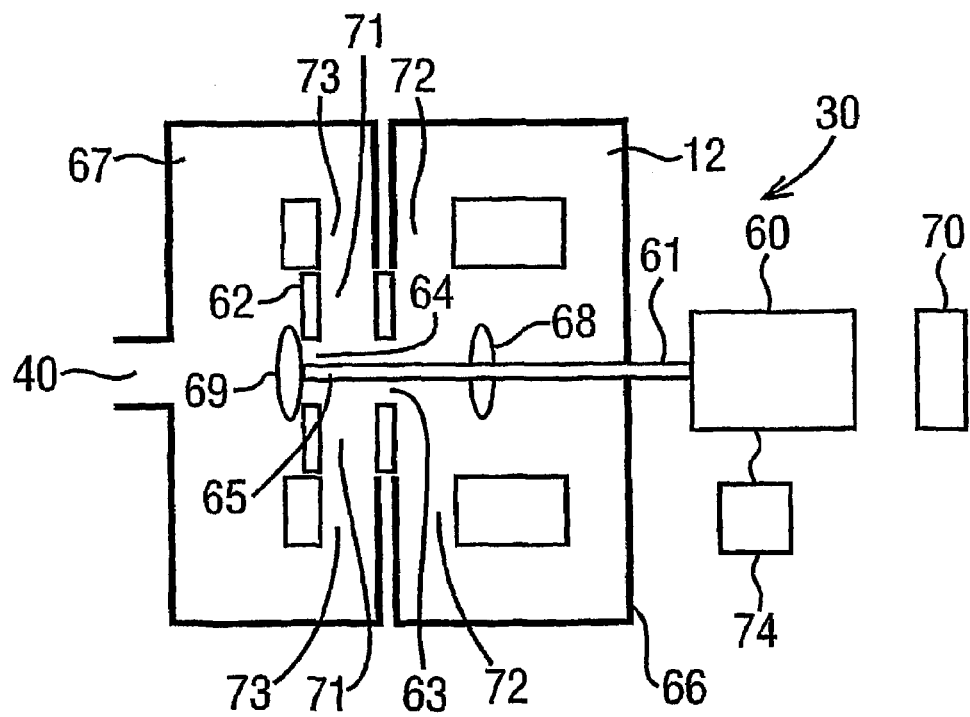
FIG. 15 is a schematic view of the portion of the blood circulation assistance device shown in FIG. 14 in a second position.

In FIGS. 14 and 15 a pump means 30 in accordance with certain embodiments of the invention is shown schematically and will now be described. The pump means 30 is a radial pump and comprises an electric motor 60 linked to a rotatable axle 61. At one end of the rotatable axle 61 is attached a circular radial centrifugal impeller 62. The impeller has intakes 63, 64, adjacent its hub 65, on each side. One intake 63 leads from a reservoir 66, the other intake 64 leads from a holding tank 67. A washer 68, 69 is provided on each side of the impeller, adjacent a respective intake 63, 64.

The impeller 62 is axially slideable from a first position (shown in FIG. 14) in which one of the washers 68 blocks the intake 63 from the reservoir 66 but the intake 64 from the holding tank 67 is clear and a second position (shown in FIG. 15) in which the other washer 69 blocks the intake 64 from the holding tank 67 but the intake 63 from the reservoir 66 is clear. An electromagnet 70 is provided to slide the axle 61 and the impeller 62 between the first and second positions.

The intakes 63, 64 lead outwardly, through the interior of the impeller 62, to discharge ports 71 at the rim of the impeller 62. Adjacent the rim of the impeller 62 are two diffusers 72, 73. One diffuser 72 leads back to the reservoir 66. The other diffuser 73 leads back to the holding tank 67. When the impeller 62 is in the first position the discharge ports 71 feed into the diffuser 72 leading to the reservoir 66 and in the second position the discharge ports 71 feed into the diffuser 73 leading to the holding tank 67.

The reservoir and holding tank contain the fluid 12, as described in the first embodiment. The holding tank 67 is in fluid communication with the bladder 10 of the blood circulation assistance device 1 via the connecting tube 40.

In use, the impeller 62 is rotated on the axle 61 at high speed by the motor 60. The impeller 62 is maintained in the first position by the electromagnet 70 so that the intake 64 from the holding tank and the diffuser 72 to the reservoir 66 are open and the intake 63 from the reservoir 66 and the diffuser to the holding tank 67 are closed. Thus the impeller 62 drives the fluid 12 from the holding tank 67 to the reservoir 66. Since the holding tank 67 is in fluid communication with the bladder 10, the pressure of fluid 12 within the bladder 10 is kept relatively low and so the bladder 10 is maintained in its contracted form.

At diastole, a signal from the control means 50 results in the electromagnet 70 sliding the axle 61 such that the impeller 62 moves to the second position. The impeller 62 continues to be rotated by the axle 61 in the same direction. Now, however, the intake 64 from the holding tank 67 and the diffuser 72 to the reservoir 66 are closed and, instead, the intake 63 from the reservoir 66 and the diffuser 73 to the holding tank 67 are open. Accordingly, the impeller 62 drives the fluid 12 from the reservoir 66 to the holding tank 67, increasing the fluid pressure in the holding tank 67 and, therefore, the fluid pressure in the bladder 10. Thus the bladder is moved into its expanded form.

Subsequently, but still during diastole, the control means 50 signals the electromagnet 70 to return the impeller to its first position and the process is repeated.

In some alternative embodiments, the pump means 30 does not comprise the holding tank 67. In these embodiments, the diffuser 73 that would otherwise lead to the holding tank 67 instead leads directly to the bladder 10. Similarly, the intake 64 that would otherwise lead from the holding tank 67 instead leads directly from the bladder 10. Thus, in these embodiments, the pump means 30 is integral with the outer cuff 11 and is directly connected to the bladder 10.

It has been determined that, in essence, the efficacy of counterpulsation is a function of the rate of blood displacement and refill flow from the section of the blood vessel in contact with the bladder 10. In other words, a high rate of change of blood flow (dQ/dt) and a rapid flow reversal of fluid to and from the bladder 10 are desirable. This is particularly important under conditions of cardiac failure which is normally characterised by an elevated heart rate (tachycardia) which limits the diastolic period. The advantage of the type of pump means 30 described above is that the direction of pumping can be reversed very rapidly because the direction of rotation of the impeller 62 does not have to be changed in order to change the direction of pumping. This is possible because the pump means comprises a radial pump and linear actuator integrated into one moving part. Longitudinal displacement of the radial pump results in alignment with either an inlet or outlet manifold. In this way, high dQ/dt and extremely rapid flow reversal of fluid to and from the bladder 10 can be achieved with an extremely compact pump means 30.

Furthermore, the pressure in the holding tank 67, and thus in the bladder 10, can be maintained for extended periods of time. This has the effect of causing a powerful, sustained compression of the blood conduit about which the bladder 10 is located to result in effective counterpulsation. In particular, a pump of this type is capable of causing the bladder 10 to move from the contracted to the expanded form in between 10 and 200 ms; maintaining the bladder 10 in the expanded form and the blood conduit compressed for between 1 and 300 ms; and returning the bladder 10 to the contracted form in 10 to 300 ms.

A further advantage of a pump means 30 of this type is that the monitoring of the cardiac cycle of the individual to whom the blood circulation assistance device 1 is fitted can be measured using the pump means. This employs the principle that the current drawn by radial pumps is inversely related to afterload. Thus, for an electrohydraulic pump means 30 as described above, coupled to an extra-aortic counterpulsator comprising an inflatable bladder 10 and an outer cuff 11, aortic pressure can be determined from the current profile in the motor 60 for the purposes of synchronisation of the blood circulation assistance device 1 with the cardiac cycle.

Thus, in some embodiments, a current monitor 74 is provided, connected to the electrical contacts that power the motor 60. The current monitor 74 measures the current to the motor 60 over time. In use of the blood circulation assistance device 1, the current to the motor 60 changes cyclically over the same time period as the cardiac cycle of the individual. In particular, as the pressure in the blood vessel of the individual falls at diastole, the electrical current supplied to the motor 60 also falls. Thus the period of diastole is determined by the current monitor 74 without the need to monitor the cardiac cycle of the individual directly. When the current monitor 74 determines that the cardiac cycle has reached diastole, the current monitor 74 signals the motor 60 to effect pumping to move the inflatable bladder 10 to the expanded form to cause counterpulsation.

In some of these embodiments of the invention, the current monitor 74 is provided in addition to the pacemaker 50 and sensor 51 that have been described above in order to serve as an integrated control means. However, in some other embodiments, the pacemaker 50 and sensor 51 are not provided and the current monitor 74 is the sole control means. In these embodiments, when the blood circulation assistance device 1 is started, the current monitor 74 does not have any starting data as to what point in the cardiac cycle has been reached. Accordingly the current monitor 74 initially signals the motor 60 to effect several test pumps on the blood vessel and measures the current during these test pumps. In response to the variation of the electrical current to the motor 60 during these test pumps, the current monitor 74 calculates the position reached in the cardiac cycle and operates as has been described previously. While the initial test pumps may not be at diastole and therefore may not cause counterpulsation, they are relatively few in number and do not cause any undesirable side-effects.

A particularly preferred pump means 30 is an Affeld pump which is described in greater detail in U.S. Pat. No. 5,346,458, which is incorporated herein by reference.

In order to effect expansion of the inflatable bladder 10 in the above described time periods, it is important that the connecting tube 40 between the pump means 30 and the bladder 10 be as short and wide as possible. Preferably the connecting tube is less than 20 mm long. This ensures that there is the shortest possible delay between the activation of the pump means and the expansion of the bladder. Furthermore, it is preferred that the connecting tube 40 be substantially rigid to ensure that it does not expand during an increase in the pressure of the fluid 12 which would result in reduced efficiency. Indeed, in a particularly preferred embodiment, the pump means 30 is located so close to the bladder 10 that no connecting tube 40 is required, the housing of the pump means 30 and the outer cuff 11 forming an integral, rigid unit. In this embodiment the pump means 30 is directly connected to the bladder 10.

It is to be appreciated that the provision of a pump means 30 having centrifugal impeller 62 which is axially moveable to effect reversal of the direction of pumping allows the pump means to be relatively small. This, in turn, allows the pump means 30 to be directly connected to the bladder 10 relatively easily, thereby minimising dead space and leading to further improvements in the dynamic response.

In some embodiments, a pacemaker 50 and a sensor 51 are not provided. Instead, the cardiac cycle of the individual to whom the blood circulation assistance device 1 is fitted is measured by a pressure sensor attached to the blood vessel on which the device 1 is located. The pressure sensor is located adjacent to the outer cuff 11 on the blood vessel and measures the pressure of blood in the blood vessel over time. The pressure sensor is connected to the pump means 30 and, when the pressure sensor detects that the cardiac cycle is at diastole, the pressure sensor signals the pump means 30 to effect pumping to cause compression of the blood vessel.

In some embodiments of the present invention, the blood circulation assistance device 1 does not comprise a bladder 10 and pump means 30. In these embodiments, a solid state compression means and mechanical driving means are provided. In certain embodiments these comprise piezoelectric materials or electrostrictive materials (i.e. materials that contract in response to an electric field) such as electrostrictive polymers.

Figure 21:
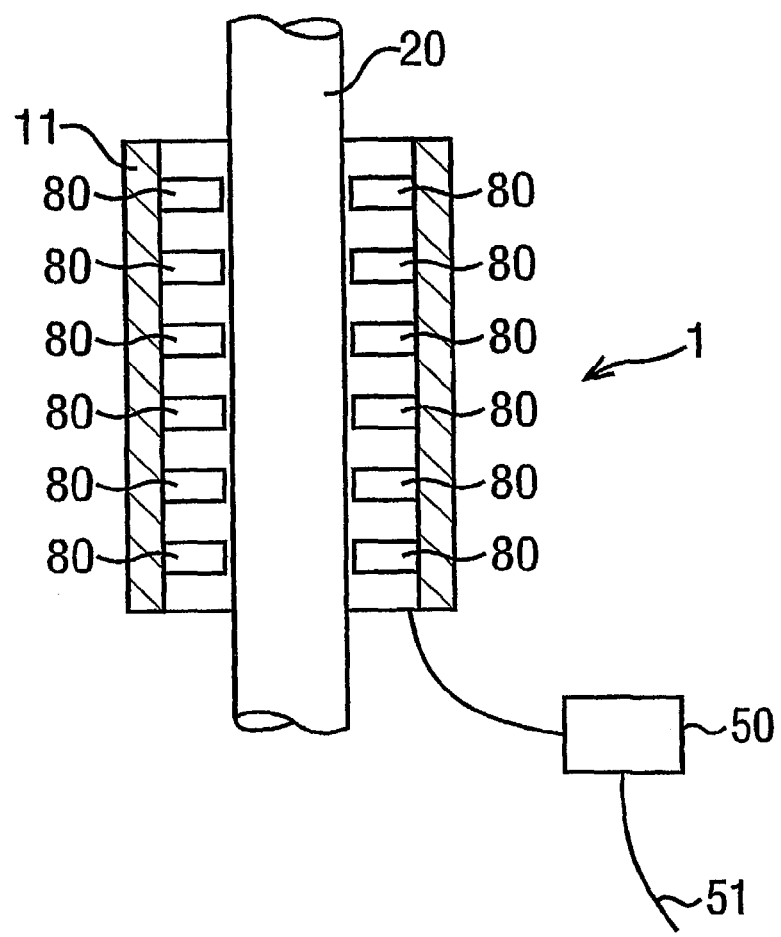
FIG. 21 is a part longitudinal cross-sectional, part schematic view of a blood circulation assistance device according to a further embodiment of the present invention.
Figure 22:
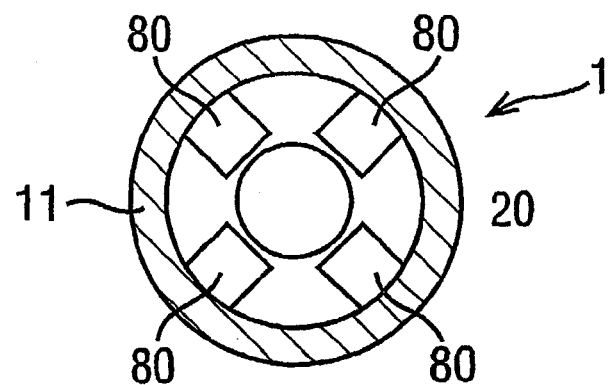
FIG. 22 is a radial cross-sectional view of the embodiment shown in FIG. 21.

Referring to FIGS. 21 and 22, one such embodiment will now be described. The blood circulation assistance device 1 comprises an outer cuff 11 that is substantially the same as the outer cuff 11 described in relation to the previous embodiments of the invention. Accordingly, the outer cuff comprises a substantially cylindrical tube. Located around the inner circumference of the outer cuff 11 are an array of radially inwardly extending compression elements 80. The compression elements 80 are arranged in four axially extending lines, spaced equidistantly about the interior circumference of the outer cuff 11, each line comprising six compression elements 80. The inner end of each compression element 80, distant from the outer cuff 11, is adjacent to the exterior of the blood conduit 20 about which the blood circulation assistance device is located.

Each of the compression elements 80 comprises a piezoelectric material which expands inwardly when an electric current is applied to the material from a contracted form to an expanded form. Each of the compression elements 80 is in electrical communication with a pacemaker 50 which, in turn, is connected to a sensor 51 as described in previous embodiments.

In use, the blood circulation assistance device 1 is located around a blood conduit 20 as has been described in the previous embodiments. Thus in certain embodiments, the outer cuff 11 comprises two separate hinged sections in order allow fitting of the cuff 11 about the blood conduit 20. Prior to diastole, an electric current is not supplied to the compression elements 80 and thus each of the compression elements 80 is in its contracted form as shown in FIG. 21. At diastole the pacemaker 50 supplies an electric current to each of the compression elements 80 thus causing the compression elements 80 to move to their expanded form. As each compression element 80 moves, it contacts and compresses the blood conduit 20. The current is maintained for a predetermined length of time, thus maintaining the blood conduit 20 in a compressed form. The pacemaker 50 then stops the electric current to the compression elements 80, in response to which compression elements 80 return to their contracted form and release the blood conduit 20 from compression. The process is then repeated in order to effect counterpulsation.

The advantage of such solid state compression means is that they are considerably more efficient in compressing the blood conduit than embodiments in which a bladder 10 and pump means 30 are used. Therefore, a smaller or longer lasting power supply can be provided. Furthermore, because there is no requirement for a pump or a motor, the blood circulation assistance device 1, itself, can be considerably smaller than is otherwise possible. In addition, in these embodiments, there is no requirement for the provision of a fluid 12 and associated hydraulic equipment and so the blood circulation assistance device 1 is more reliable.

In some variations of these embodiments, the pacemaker 50 does not supply an electric current to all of the compression elements 80 in the array simultaneously. Instead, the electric current is initially supplied to the four compression elements 80 at one end of the outer cuff 11 in order that they move to the expanded form and compress the blood conduit 20. Subsequently, the adjacent four compression elements 80, further along their respective lines in the array, are supplied with current so that they move to the expanded form and compress the blood conduit 20. This process is then continued with each set of four compression elements being moved to the expanded form until all of the compression elements 80 in the array are in the expanded form. Thus the compression elements 80 are activated sequentially to cause peristaltic compression of the blood conduit 20. This provides a pulsatile motion to the blood in the blood conduit 20 as it is compressed.

It is to be appreciated that, in these embodiments of the invention, it is advantageous that the compression elements 80 expand as much as possible when they move from the contracted to the expanded form. This ensures that the blood conduit 20 is compressed as much as possible and a large volume of blood in the blood conduit 20 is displaced. It is known in the art to provide a flat strip that comprise a layer of piezoelectric material and a layer of another material such that, upon the application of an electric current, the layer of the piezoelectric material expands relative to the other layer causing a bending of the layers and a linear extension of the strip. The distance that the strip extends upon the application of an electric current can be increased if the strip is initially wound into the form of a helix. In this form, when the electric current is supplied to the piezoelectric material, the helix expands axially a distance greater than the linear extension of the flat strip. Furthermore, the helix can, itself, be wound into a larger helix whose axial extension on the application of an electric current is even greater than the axial extension of the initial helix. This process can be repeated many times, with each helix being wound into a larger helix having a greater axial extension than the previous helix. Thus a compression element 80 having the necessary expansion in order to compress the blood conduit sufficiently can be made by constructing the compression element 80 from a piezoelectric strip wound into successive helices enough times to create the required axial extension upon the application of an electric current.

Further details of the piezoelectric and electrostrictive materials that can be used in connection with these embodiments of the invention are disclosed in the following documents, each of which is incorporated herein by reference. WO-A-01/47318, GB-A-2322232, WO-A-01/47041, U.S. Pat. Nos. 6,111,818, 5,215,446, 5,136,201, 4,633,120, 6,084,321, 6,249,076, 6,109,852, WO-A-92/10916, and WO-A-99/17929.

In embodiments of the present invention, the blood circulation assistance device 1, alone, is generally sufficient to assist an individual's circulation by effecting counterpulsation. Therefore, additional assistance for the individual's blood circulation (such as copulsation) is not usually required once the blood circulation assistance device 1 has been implanted.

EXAMPLES

Example 1

Typical early prototype devices described above have been evaluated in a series of in vitro models operating under static and dynamic modes[7] using a cardiovascular simulator equipped with an artificial aorta[8] (supplied by Institute of Biomedical Technology Hydraulics Laboratory, University of Ghent, NL). The blood circulation assistance device under test was an extra-aortic counterpulsator having two inflatable bladders. The extra-aortic counterpulsator had a length of 50 mm, internal diameter of 33 mm and a total bladder volume of 15 ml. The extra-aortic counterpulsator was capable of displacing 20 ml blood at each compression.

The results summarised in the table below from the static model were compared with the performance of intra aortic balloon counterpulsation (Datascope System 90 equipped with a 40 cc intra aortic balloon: 9.5 French Catheter Scale; cat nos. 0334-00-1377-03 R1).

|  | Perfusion (Area) mmHg · s | Change | % Change |
| --- | --- | --- | --- |
| Reference | 46.3 |  |  |
| IAB Assisted (comparison) | 62.3 | 10.0 | 34.6 |
| Reference | 47.1 |  |  |
| Extra-aortic counterpulsator | 56.7 | 9.6 | 20.4 |

It is to be noted, with respect to the above results, that the intra-aortic balloon tested displaces 40 ml of blood on each compression whereas the extra-aortic counterpulsator displaces only 20 ml of blood on each compression. Therefore, the extra-aortic counterpulsator actually provides a greater percentage change in perfusion per ml of blood displaced than the intra-aortic balloon.

Figure 16:
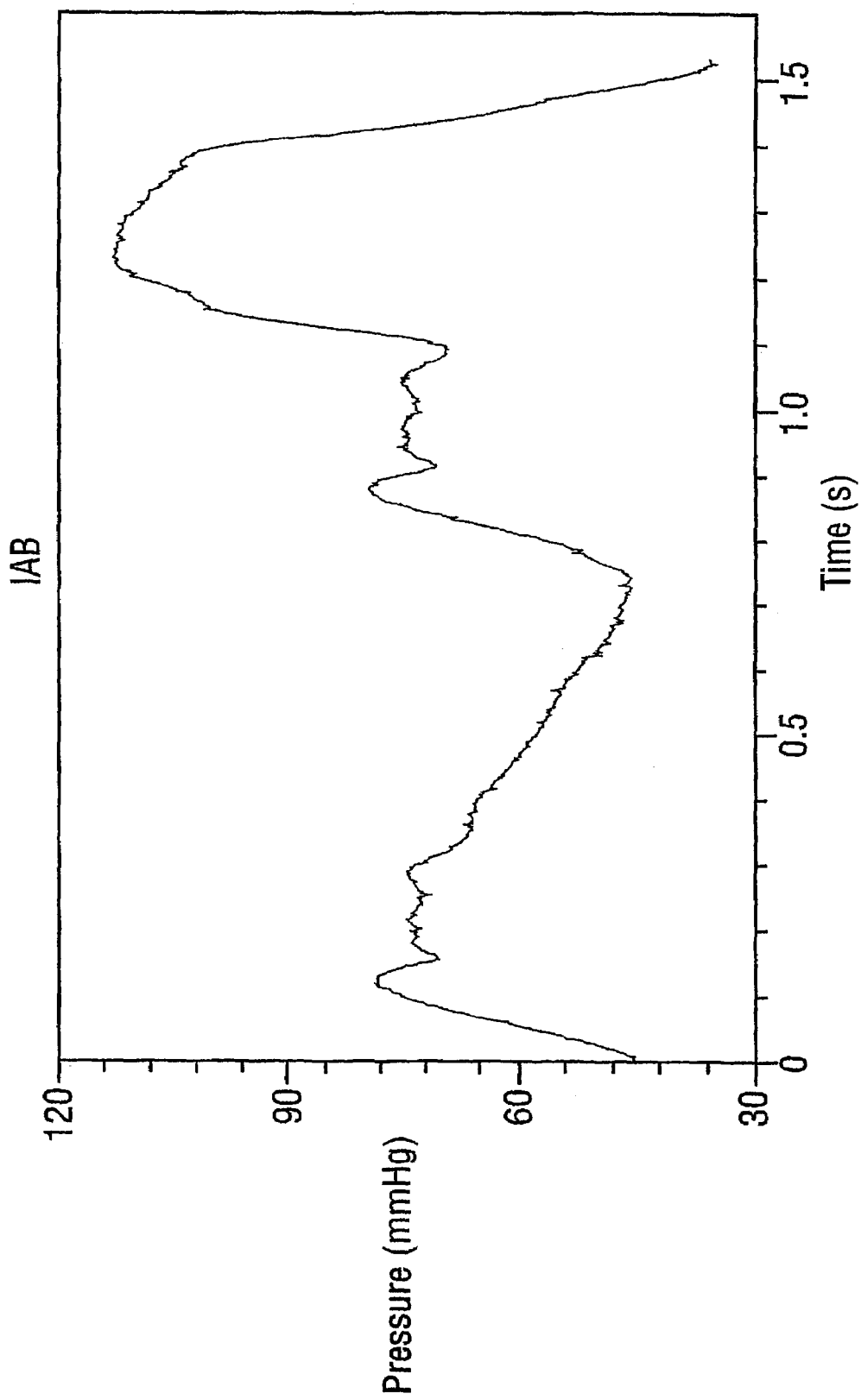
FIG. 16 is a pressure output graph for an intra-aortic balloon in Example 1.
Figure 17:
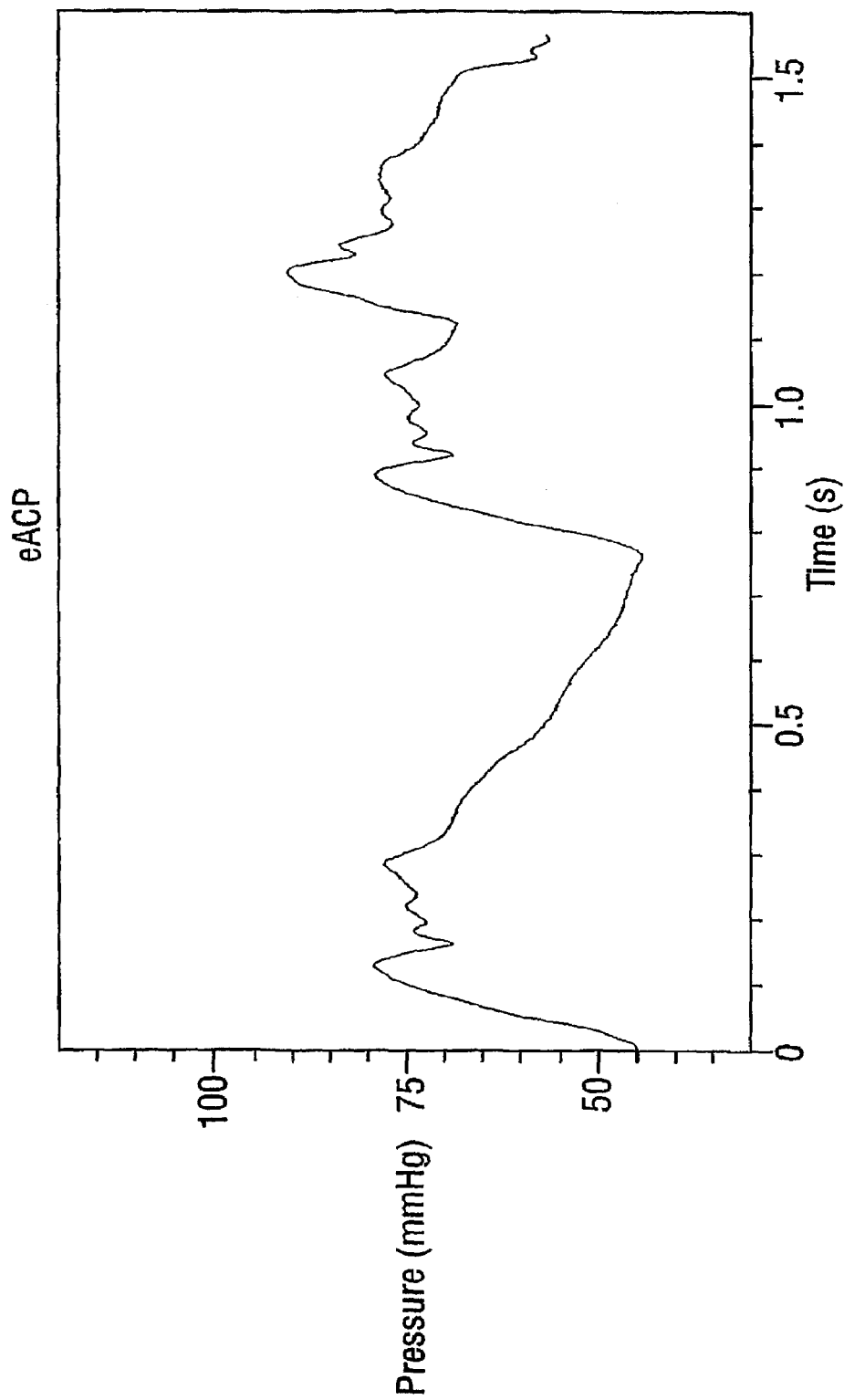
FIG. 17 is a pressure output graph for an extra-aortic counterpulsator in accordance with one embodiment of the present invention in Example 1.

The pressure output graphs of these experiments are shown as FIG. 16 for the intra-aortic balloon (IAB) and FIG. 17 for the extra-aortic counterpulsator. As can be seen from the pressure graphs, the extra-aortic counterpulsator causes an increase in pressure at diastole to a similar extent as the intra-aortic balloon.

Example 2

Figure 18:
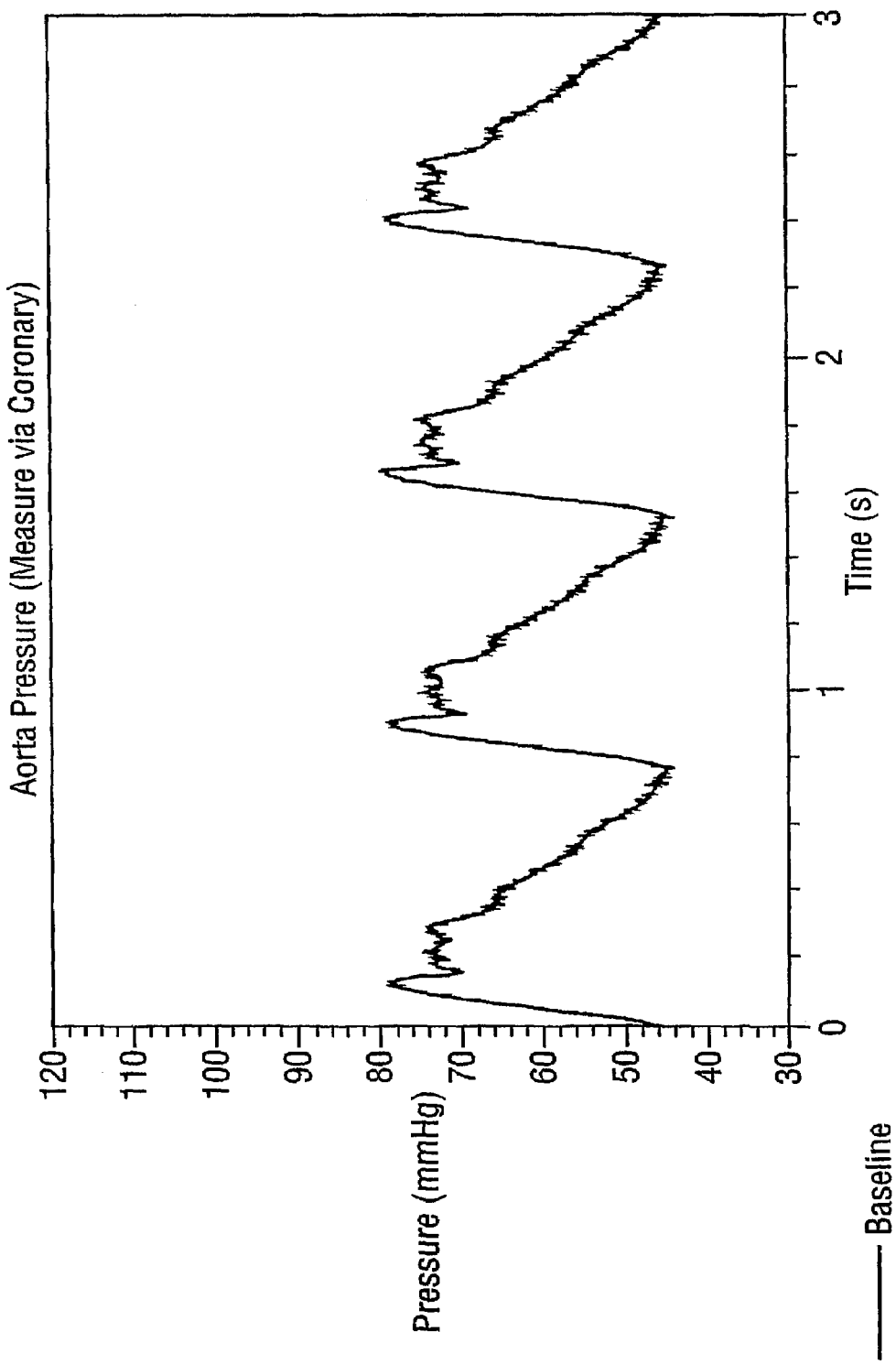
FIG. 18 is a pressure time curve measured on a cardiovascular simulator in Example 2.

In this example, the intra-aortic balloon used in Example 1 was compared with a single bladder extra-aortic counterpulsator under dynamic conditions. The extra-aortic counterpulsator had a length of 50 mm, an internal diameter of 33 mm and a total bladder volume of 40 ml. The extra-aortic counterpulsator displaced 40 ml of blood on each compression. The intra-aortic balloon and the extra-aortic counterpulsator were signalled to compress on alternate diastoles of the simulated cardiac cycle. The results of the experiments are shown in the table below. Furthermore, pressure time curves measured on the cardiovascular simulator are shown as follows: without circulation assistance (FIG. 18); with intra-aortic balloon assistance (FIG. 19) and with extra-aortic counterpulsator (EAC) assistance (FIG. 20).

| Type of Counterpulsation | Base pressure P (mm Hg) | Peak pressure P (mm Hg) | Area increase (mm Hg.s) | % area increase | Notes |
| --- | --- | --- | --- | --- | --- |
| No Counterpulsation (i.e. no EAC or IAB fitted) | 69 | 126 | 0 | 0% | 70 bpm; $T_F$ 3.5 l/min |
| IAB-40 ml displaced: 94 ms delay] | 79 | 136 | 110 | 15% | 70 bpm; $T_F$ 3.7 l/min |
| EAC-40 ml displaced: 30 ms delay] | 73 | 130 | 118 | 30% | 70 bpm; $T_F$ 3.7 l/min | bpm = beats per minute
$T_F$ = total coronary flow (litres per minute)

Figure 19:
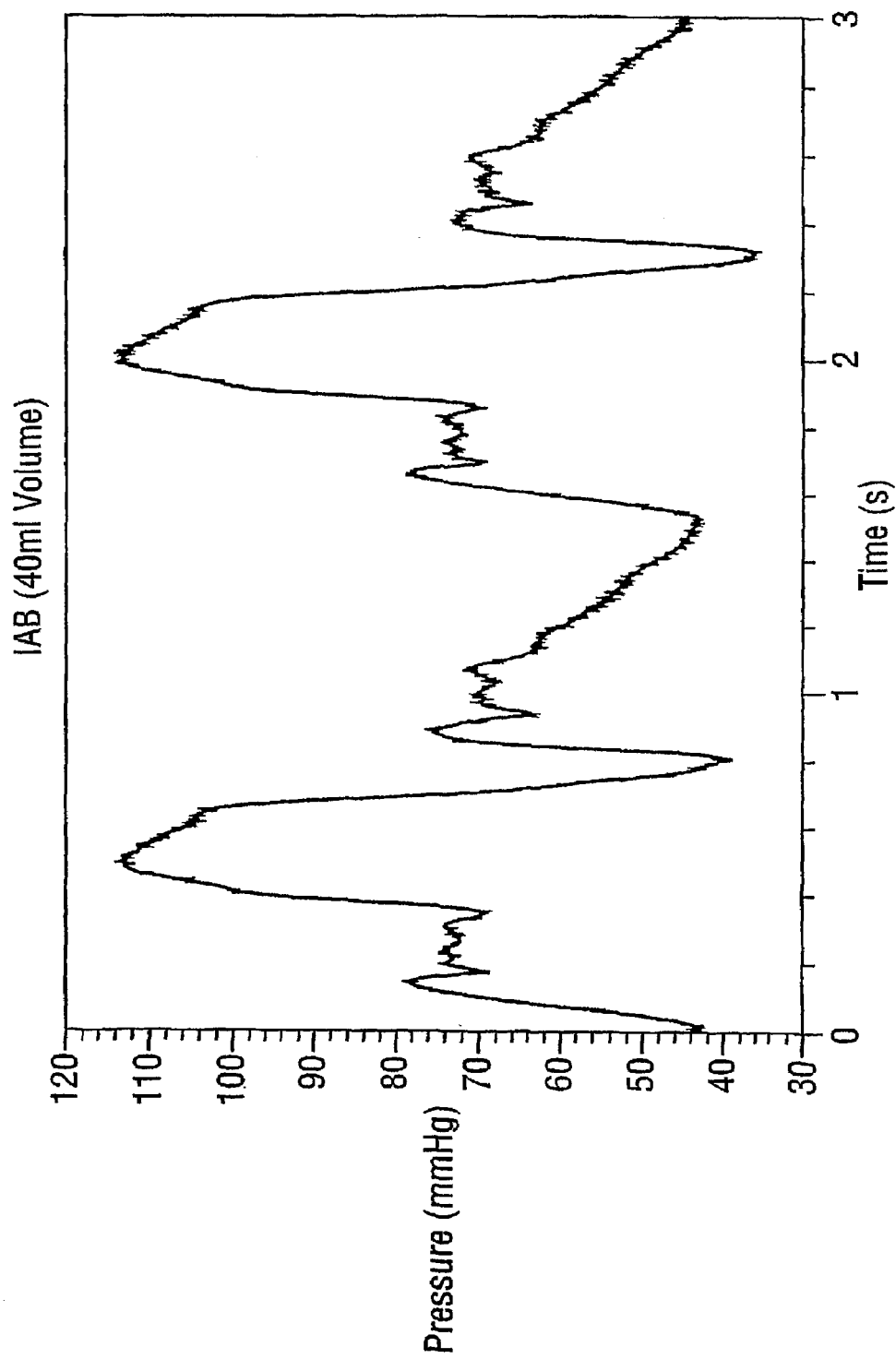
FIG. 19 is a pressure time curve measured on a cardiovascular simulator with intra-aortic balloon assistance in Example 2.
Figure 20:
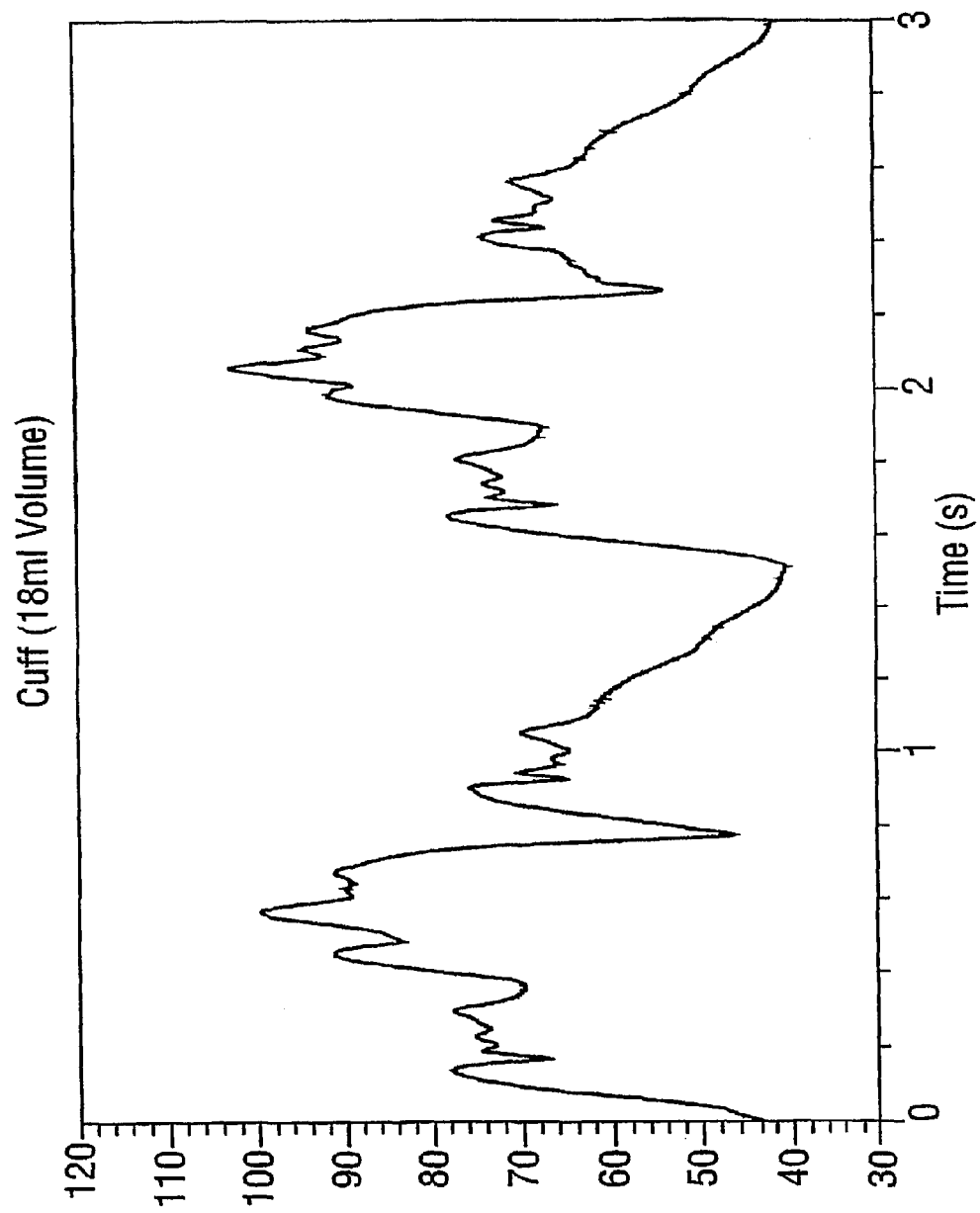
FIG. 20 is a pressure time curve measured on a cardiovascular simulator with extra-aortic counterpulsator assistance in Example 2.

As can be seen on comparison of FIGS. 19 and 20, the extra-aortic counterpulsator was capable of effecting similar increases in pressure at diastole as the intra-aortic balloon. Accordingly, this example shows that the extra-aortic counterpulsator is able to effect counterpulsation to an extent sufficient to have a positive effect on a patient in need of such treatment.

References

[1] Clauss R H; J Thorac. Cardiovasc.Surg. 42, p447 (1961)
[2] Moulopoulos S D et al; 'Diastolic balloon pump assistance and early surgery in cardiogenic shock' Am.Heart J. 63 p669 (1962)
[3] Mundth3 E D., Assisted Circulation in Gibbon's Surgery of the Chest, Editors Sabiston D C and Spencer F C, Saunders p1490–1514 (1983)
[4] Hayward M P et al; supra WO 92/08500
[5] Fischer E I; Ann.Thorac.Surg., 60, p417–421 (1995)
[6] Carpenter et al 'Myocardial Substitution with a Stimulated Skeletal Muscle: First Successful Clinical Case' The Lancet p1267 (June 1985)
[7] Segers P, Dubois F, Wachter De, Verdonck P 'Role and Relevancy of a Cardiovascular Simulator' Cardiovascular Engineering, 3, p48 (1998)
[8] Verdonck P University of Ghent, Institute of Biomedical Technology Hydraulics Laboratory.

What is claimed is:

1. A blood circulation assistance device, for location around a blood conduit, the device comprising:
   at least one inflatable bladder moveable between a contracted form and an expanded form, for compressing the blood conduit to provide counterpulsation;
   pump means in fluid communication with the at least one inflatable bladder for moving the at least one inflatable bladder from the contracted form to the expanded form, the pump means comprising a centrifugal impeller rotatable about an axis to effect pumping, the impeller being moveable axially between first and second positions to effect a reversal of the direction of pumping;
   control means in communication with the pump means, the control means being capable of monitoring the cardiac cycle of an individual and triggering the pump means to move the at least one inflatable bladder to the expanded form at diastole; and
   an outer cuff, surrounding at least a portion of the at least one inflatable bladder, providing an outer limiting extent to the movement of the at least one inflatable bladder,
   the at least one inflatable bladder being locatable between the blood conduit and the outer cuff such that, in its expanded form, the at least one inflatable bladder presses against the outer limiting extent of the outer cuff to compress the blood conduit.

2. A blood circulation assistance device according to claim 1 wherein the pump means is connected in fluid communication with the at least one inflatable bladder by a substantially rigid tube.

3. A blood circulation assistance device according to claim 2 wherein the substantially rigid tube is less than 20 mm long.

4. A blood circulation assistance device according to claim 1 wherein the pump means is located adjacent the at least one inflatable bladder such that the pump is directly connected to the at least one inflatable bladder.

5. A blood circulation assistance device according to claim 1 further comprising a fluid to effect fluid communication between the pump means and at least one inflatable bladder wherein the fluid is a liquid.

6. The blood circulation assistance device according to claim 5, wherein the liquid comprises a viscosity of up to $10^3$ Pas.

7. The device of claim 6 wherein the liquid has a viscosity in the range of 1 Pa to $10^3$ Pas.

8. A blood circulation assistance device according to claim 1 wherein the pump means further comprise first and second diffusers for receiving fluid from the impeller, the centrifugal impeller being axially moveable relative to the diffusers between the first position in which the impeller is in fluid communication with the first diffuser and the second position in which the impeller is in fluid communication with the second diffuser to effect a reversal of the direction of pumping.

9. A blood circulation assistance device according to claim 8 wherein the pump means further comprise first and second intakes for supplying fluid to the impeller, the intakes being located such that, in the first position, the centrifugal impeller is in fluid communication with the first intake and in the second position, the impeller is in fluid communication with the second intake.

10. A blood circulation assistance device according to claim 1 wherein the pump means further comprise an electromagnet for sliding the impeller between the first and second positions.

11. A blood circulation assistance device according to claim 1 wherein there is a plurality of inflatable bladders.

12. A blood circulation assistance device according to claim 11 wherein the inflatable bladders are configured to be locatable symmetrically about the axis of the blood conduit.

13. A blood circulation assistance device according to claim 1 wherein the at least one inflatable bladder is made from a material having a tensile strength in a range from 15 to 35 MPas.

14. The blood circulation assistance device of claim 13 wherein the at least one inflatable bladder is made from a material having a tensile strength in a range from 20 to 30 MPas.

15. The blood circulation assistance device of claim 13 wherein the at least one inflatable bladder is made from a material having a tensile strength of about 25 MPas.

16. A blood circulation assistance device according to claim 1 wherein the at least one inflatable bladder is made from a material having a Modulus at 100% elongation in a range from 2 to 6 MPas.

17. The blood circulation assistance device of claim 16 wherein the bladder is made from a material having a Modulus at 100% elongation in a range from 2.5 to 5 MPas.

18. The blood circulation assistance device of claim 16 wherein the bladder is made from a material having a Modulus at 100% elongation of about 2.64 MPas.

19. A blood circulation assistance device according to claim 1 wherein the at least one inflatable bladder is made from a material having a modulus at 300% elongation in a range from 4 to 10 MPas.

20. A blood circulation assistance device according to claim 19 wherein the bladder is made from a material having a Modulus at 300% elongation in a range from 6 to 7 MPas.

21. A blood circulation assistance device according to claim 19 wherein the bladder is made from a material having a Modulus at 300% elongation of about 6.23 MPas.

22. A blood circulation assistance device according to claim 1 further comprising at least one plate connected to the at least one inflatable bladder, the at least one plate being locatable adjacent the blood conduit such that when the at least one inflatable bladder is in its expanded form the at least one plate compresses the blood conduit.

23. A blood circulation assistance device according to claim 22 wherein the device comprises two opposing plates, locatable on either side of the blood conduit.

24. A blood circulation assistance device according to claim 1 wherein the outer cuff is a substantially rigid shell.

25. A blood circulation assistance device according to claim 24 wherein the cross section of the outer cuff has an incomplete perimeter bounded by two opposing outer edges along the length of the cuff such that the device is locatable to surround a portion of the circumference of the blood conduit.

26. A blood circulation assistance device according to claim 25 further comprising a substantially rigid panel attachable to the opposing outer edges of the outer cuff such that the rigid panel co-operates with the outer cuff to define the outer limiting extent to the movement of the at least one inflatable bladder.

27. A blood circulation assistance device according to claim 25 wherein the opposing outer edges of the outer cuff are attachable to a bone such that the bone co-operates with the outer cuff to define the outer limiting extent to the movement of the at least one inflatable bladder.

28. A blood circulation assistance device according to claim 1 wherein the outer cuff has a substantially circular cross-section and is locatable to surround the whole circumference of the blood conduit.

29. A blood circulation assistance device according to claim 28 wherein the outer extent of the outer cuff defines a plane, the outer cuff comprising two portions connected by a hinge perpendicular to the plane such that the outer cuff is moveable from an open configuration for positioning of the device about a blood conduit to a closed configuration for the device to effect counterpulsation of the blood conduit.

30. A blood circulation assistance device according to claim 29 wherein the outer cuff further comprises a clip for locking the two portions of the outer cuff in the closed configuration.

31. A blood circulation assistance device according to claim 1 further comprising a cushion locatable between the blood conduit and the at least one inflatable bladder for cushioning the blood conduit when the at least one inflatable bladder moves to the expanded form.

32. A blood circulation assistance device according to claim 31 wherein the cushion comprises a Teflon™ pad.

33. A blood circulation assistance device according to claim 1 wherein the pump means is operable to move the at least one inflatable bladder from the contracted form to the expanded form in 10 to 200 ms, to remain in the expanded form for between 1 and 300 ms and to return to the contracted form in 10 to 400 ms in order to effect counterpulsation.

34. A blood circulation assistance device according to claim 1 wherein the device is capable of displacing up to 80 ml of blood from the blood conduit when the at least one inflatable bladder moves from the contracted form to the expanded form about a blood conduit.

35. A blood circulation assistance device according to claim 34 wherein the device is configured to displace blood in a range of 15 ml to 40 ml.

36. A blood circulation assistance device according to claim 1 wherein the blood conduit is an artificial blood conduit.

37. A blood circulation assistance device according to claim 36 wherein the artificial blood conduit is a vascular shunt.

38. A blood circulation assistance device according to claim 37 wherein the diameter of the vascular shunt tapers from one end of the shunt to the other end.

39. A blood circulation assistance device according to claim 36 wherein the artificial blood conduit is integral to the blood circulation assistance device.

40. A blood circulation assistance device according to claim 1 wherein the control means comprise a pacemaker.

41. A blood circulation assistance device according to claim 1 wherein the pump means is powered electrically, the control means comprising means for monitoring the current to the pump means.

42. A method of providing counterpulsation to the blood circulation of an individual comprising the steps of:
providing a blood circulation assistance device comprising: at least one inflatable bladder, moveable between an expanded and a contracted form; pump means, in fluid communication with the at least one inflatable bladder, for moving the at least one inflatable bladder from the contracted form to the expanded form; the pump means comprising a centrifugal impeller rotatable about an axis to effect pumping, the impeller being moveable axially between first and second positions to effect a reversal of the direction of pumping; and an outer cuff, surrounding at least a portion of the at least one inflatable bladder, and providing an outer limiting extent to the movement of the at least one inflatable bladder;
locating the outer cuff about a blood conduit in the individual, the at least one inflatable bladder being between the blood conduit and the outer cuff;
monitoring the cardiac cycle of the individual; and
effecting counterpulsation on the blood conduit by operating the pump means to move the at least one inflatable bladder from the contracted form to the expanded form at diastole, the at least one inflatable bladder thus pressing against the outer limiting extent of the outer cuff and compressing the blood conduit.

43. A method according to claim 42 wherein the blood circulation assistance device further comprises control means in communication with the pump means, the control means being capable of monitoring the cardiac cycle of an individual and triggering the pump means to move the at least one inflatable bladder to the expanded form at diastole, and wherein the at least one inflatable bladder is locatable between the blood conduit and the outer cuff such that, in its expanded form, the at least one inflatable bladder presses against the outer limiting extent of the outer cuff to compress the blood conduit.

44. A method according to claim 42 wherein the outer cuff has a substantially circular cross-section and is locatable to surround the whole circumference of the blood conduit, and wherein the outer extent of the outer cuff defines a plane, the outer cuff comprising two portions connected by a hinge perpendicular to the plane such that the outer cuff is movable from an open configuration for positioning of the device about a blood conduit to a closed configuration for the device to effect counter pulsation of the blood conduit, and wherein the step of locating the outer cuff about the blood conduit comprises:
moving the outer cuff into the open configuration;
positioning the outer cuff about the blood conduit; and
moving the outer cuff into the closed configuration.

45. A method according to claim 44 wherein the outer cuff further comprises a clip for locking the two portions of the outer cuff in the closed configuration, and wherein the step of locating the outer cuff about the blood conduit further comprises the step of, after moving the outer cuff into the closed configuration:
locking the two portions of the outer cuff with the clip.

46. A method according to claim 42 wherein the outer cuff is in a substantially rigid shell, the cross section of the outer cuff has an incomplete perimeter bounded by two opposing outer edges along the length of the cuff such that the device is locatable to surround a portion of the circumference of the blood conduit, wherein the blood circulation assistance device further comprises a substantially rigid panel attachable to the opposing outer edges of the outer cuff such that the rigid panel cooperates with the outer cuff to define the outer limiting extent to the movement of the at least one inflatable bladder, and wherein the step of locating the outer cuff about the blood conduit comprises:

inserting the blood conduit through the opposing outer edges of the outer cuff; and attaching the substantially rigid panel to the opposing outer edges of the outer cuff so that the whole circumference of the blood conduit is surrounded by the outer limiting extent defined by the outer cuff and the substantially rigid panel.

47. A method according to claim 42 wherein the outer cuff is a substantially rigid shell, the cross section of the outer cuff has an incomplete perimeter bounded by two opposing outer edges along the length of the cuff such that the device is locatable to surround a portion of the circumference of the blood conduit, the opposing outer edges of the outer cuff are attachable to a bone such that the bone cooperates with the outer cuff to define the outer limiting extent to the movement of the at least one inflatable bladder, and wherein the step of locating the outer cuff about the blood conduit comprises:

inserting the blood conduit through the opposing outer edges of the outer cuff; and attaching the opposing outer edges of the outer cuff to a bone in the individual so that the whole circumference of the blood conduit is surrounded by the outer limiting extent defined by the outer cuff and the bone.

48. A method according to claim 47 wherein the bone is a vertebra.

49. A method according to claim 42 wherein the blood conduit is an artificial conduit, and further comprising the steps of severing a blood vessel in the individual to provide two ends of the blood vessel and attaching either end of the artificial blood conduit to a respective end of the blood vessel.

50. A method according to claim 49 further comprising the step of removing a section of the blood vessel prior to attaching either end of the artificial blood conduit to the respective ends of the blood vessel.

51. A method according to claim 49 wherein the blood vessel is the aorta of the individual.

52. A method according to claim 51 wherein the blood vessel is the ascending aorta.

53. A method according to claim 51 wherein the blood vessel is the descending aorta.

54. A method according to claim 42 using the blood circulation assistance device of claim 29 further comprising the steps of grafting either end of the vascular shunt to a blood vessel in the individual such that blood passes through the vascular shunt in parallel with the blood vessel.

55. A method according to claim 42 wherein the blood conduit is a blood vessel in the individual.

56. A method according to claim 55 further comprising the step of inserting a synthetic patch into the wall of the blood vessel to increase the diameter of the blood vessel.

57. A method according to claim 42 wherein no copulsation is performed.

58. A blood circulation assistance device, for location around a blood conduit, the device comprising:

solid state compression means moveable between a contracted form and an expanded form, for compressing the blood conduit to provide counterpulsation, control means in communication with the solid state compression means, the control means being capable of monitoring the cardiac cycle of an individual and triggering the solid state compression means to move to the expanded form at diastole; and an outer cuff surrounding at least a portion of the solid state compression means, providing an outer limiting extent to the movement of the solid state compression means, the solid state compression means being locatable between the blood conduit and the outer cuff such that, in its expanded form, the solid state compression means presses against the outer limiting extent of the outer cuff to compress the blood conduit.

59. A blood circulation assistance device according to claim 58 wherein the solid state compression means comprises at least one piezoelectric and/or electrostrictive compression elements.

60. A blood circulation assistance device according to claim 58 wherein the solid state compression means comprises an array of compression elements moveable from the contracted to the expanded form.

61. A blood circulation assistance device according to claim 60 wherein the compression elements in the array are moveable to the expanded form sequentially so as to effect peristaltic compression of the blood conduit.

* * * * *